(12) United States Patent
McLain

(10) Patent No.: US 11,712,267 B2
(45) Date of Patent: Aug. 1, 2023

(54) TILTING TANG CANNULA DEPTH LIMITER

(71) Applicant: Cilag GmbH International, Zug (CH)

(72) Inventor: Cameron D. McLain, Deer Park, OH (US)

(73) Assignee: Cilag GmbH International, Zug (CH)

( * ) Notice: Subject to any disclaimer, the term of this patent is extended or adjusted under 35 U.S.C. 154(b) by 194 days.

(21) Appl. No.: 17/213,426

(22) Filed: Mar. 26, 2021

(65) Prior Publication Data

US 2021/0338283 A1 Nov. 4, 2021

Related U.S. Application Data

(60) Provisional application No. 63/018,652, filed on May 1, 2020.

(51) Int. Cl.
*A61B 17/34* (2006.01)
*A61B 90/00* (2016.01)

(52) U.S. Cl.
CPC ...... *A61B 17/3494* (2013.01); *A61B 17/3423* (2013.01); *A61B 90/03* (2016.02); *A61B 2090/036* (2016.02)

(58) Field of Classification Search
CPC ............ A61B 17/3494; A61B 17/3423; A61B 17/3417; A61B 17/3462; A61B 17/3421;
(Continued)

(56) References Cited

U.S. PATENT DOCUMENTS 3,817,251 A 6/1974 Hasson
4,699,616 A 10/1987 Nowak et al.
(Continued)

FOREIGN PATENT DOCUMENTS

AU 702882 B2 3/1993
CN 106344126 B 2/2019
(Continued)

OTHER PUBLICATIONS

International Search Report and Written Opinion dated Jul. 22, 2021, for International Application No. PCT/EP2021/061421, 15 pages.

(Continued)

*Primary Examiner* — Tan-Uyen T Ho
*Assistant Examiner* — Regina Vahey
(74) *Attorney, Agent, or Firm* — Frost Brown Todd LLP

(57) ABSTRACT

A depth limiter configured for use with a surgical cannula includes an annular base having a boss that extends about a longitudinal axis and has a boss lumen configured to receive the surgical cannula. A latch arm coupled with the annular base overlies the boss and includes an arm opening configured to align with the boss lumen to receive the surgical cannula. The latch arm is movable relative to the annular base between a release position and a lock position. In the release position the arm opening is positioned coaxially with the boss lumen such that the latch arm is configured to permit longitudinal movement of the depth limiter along the surgical cannula. In the lock position the arm opening is positioned non-coaxially with the boss lumen such that the latch arm is configured to inhibit longitudinal movement of the depth limiter along the surgical cannula.

20 Claims, 19 Drawing Sheets

(58) Field of Classification Search
CPC .............. A61B 90/03; A61B 2090/036; A61B 2090/033; A61B 2017/00407; A61B 2017/348; A61M 5/321
See application file for complete search history.

(56) References Cited

U.S. PATENT DOCUMENTS

| | | | |
|---|---|---|---|
| 5,002,557 A | 3/1991 | Hasson | |
| 5,147,316 A | 9/1992 | Castillenti | |
| 5,215,531 A | 6/1993 | Maxson et al. | |
| D338,270 S | 8/1993 | Stephens et al. | |
| 5,256,147 A | 10/1993 | Vidal et al. | |
| 5,257,975 A | 11/1993 | Foshee | |
| 5,263,939 A | 11/1993 | Wortrich | |
| 5,267,970 A | 12/1993 | Chin et al. | |
| 5,290,249 A | 3/1994 | Foster et al. | |
| 5,364,372 A | 11/1994 | Danks et al. | |
| D354,562 S | 1/1995 | Medema | |
| 5,540,675 A | 7/1996 | Hasson | |
| 5,697,913 A | 12/1997 | Sierocuk et al. | |
| 5,792,135 A | 8/1998 | Madhani et al. | |
| 5,800,451 A | 9/1998 | Buess et al. | |
| 5,817,061 A | 10/1998 | Goodwin et al. | |
| 5,833,666 A | 11/1998 | Davis et al. | |
| 5,836,913 A | 11/1998 | Orth et al. | |
| 5,855,566 A | 1/1999 | Dunlap et al. | |
| 5,951,588 A | 9/1999 | Moenning | |
| 5,957,888 A | 9/1999 | Hinchliffe | |
| 6,432,085 B1 | 8/2002 | Stellon et al. | |
| 6,451,041 B1 | 9/2002 | Moenning et al. | |
| 6,632,197 B2 | 10/2003 | Lyon | |
| 6,638,265 B1 | 10/2003 | Ternamian | |
| 6,808,492 B2 | 10/2004 | Snyder | |
| 7,235,064 B2 | 6/2007 | Hopper et al. | |
| 7,981,092 B2 | 7/2011 | Duke | |
| 8,147,453 B2 | 4/2012 | Albrecht et al. | |
| 8,226,553 B2 | 7/2012 | Shelton, IV et al. | |
| 8,251,900 B2 | 8/2012 | Ortiz et al. | |
| 8,287,503 B2 | 10/2012 | Albrecht et al. | |
| 8,479,969 B2 | 7/2013 | Shelton, IV | |
| 8,568,362 B2 | 10/2013 | Moreno, Jr. et al. | |
| 8,573,465 B2 | 11/2013 | Shelton, IV | |
| 8,579,807 B2 | 11/2013 | Moreno, Jr. et al. | |
| 8,636,686 B2 | 1/2014 | Minnelli et al. | |
| 8,690,831 B2 | 4/2014 | Duke | |
| 8,783,541 B2 | 7/2014 | Shelton, IV et al. | |
| 8,800,838 B2 | 8/2014 | Shelton, IV | |
| 8,939,946 B2 | 1/2015 | Albrecht et al. | |
| 9,259,238 B2 | 2/2016 | Albrecht et al. | |
| 9,522,265 B2 | 12/2016 | Pravong et al. | |
| 10,327,805 B2 | 6/2019 | Hibner et al. | |
| 10,327,809 B2 | 6/2019 | Buyda et al. | |
| 10,792,069 B2 | 10/2020 | Hall et al. | |
| 10,820,924 B2 | 11/2020 | Hall et al. | |
| 2003/0105431 A1* | 6/2003 | Howell .............. | A61M 5/3273 604/164.08 |
| 2005/0113856 A1 | 5/2005 | Epstein et al. | |
| 2005/0165432 A1 | 7/2005 | Heinrich | |
| 2007/0225643 A1 | 9/2007 | Hopper et al. | |
| 2009/0182282 A1 | 7/2009 | Okihisa et al. | |
| 2010/0010449 A1 | 1/2010 | Leibowitz et al. | |
| 2010/0057010 A1 | 3/2010 | Göransson | |
| 2013/0060084 A1 | 3/2013 | Fouts et al. | |
| 2014/0066953 A1 | 3/2014 | Keating et al. | |
| 2016/0015423 A1 | 1/2016 | Ravikumar et al. | |
| 2017/0311932 A1 | 11/2017 | Rebellino | |
| 2018/0199959 A1 | 7/2018 | Lee | |
| 2018/0206883 A1 | 7/2018 | McIntyre et al. | |
| 2018/0214140 A1 | 8/2018 | Nock et al. | |
| 2019/0000496 A1 | 1/2019 | Shelton, IV et al. | |
| 2019/0083071 A1 | 3/2019 | Rebellino et al. | |
| 2019/0150900 A1 | 5/2019 | Choung et al. | |
| 2019/0254703 A1 | 8/2019 | Ciampini et al. | |
| 2019/0254704 A1 | 8/2019 | Buyda et al. | |
| 2019/0314561 A1* | 10/2019 | Rhee .................. | A61B 17/3496 |
| 2019/0380742 A1 | 12/2019 | Hall et al. | |
| 2021/0338269 A1 | 11/2021 | Scott et al. | |
| 2021/0338272 A1 | 11/2021 | Muthuchidambaram et al. | |
| 2021/0338273 A1 | 11/2021 | Vijayachandran et al. | |
| 2021/0338274 A1 | 11/2021 | Scott et al. | |
| 2021/0338275 A1 | 11/2021 | Vijayachandran | |
| 2021/0338276 A1 | 11/2021 | Scott | |
| 2021/0338278 A1 | 11/2021 | Scott et al. | |
| 2021/0338281 A1 | 11/2021 | Mozloom, Jr. et al. | |
| 2021/0338282 A1 | 11/2021 | Vijayachandran | |
| 2021/0338371 A1 | 11/2021 | Harris et al. | |

FOREIGN PATENT DOCUMENTS

| | | |
|---|---|---|
| DE | 202007001745 U1 | 4/2007 |
| EP | 2174602 A1 | 4/2010 |
| EP | 3210553 B1 | 10/2019 |
| WO | WO 1999/052457 A1 | 10/1999 |
| WO | WO 2004/032756 A2 | 4/2004 |
| WO | WO 2014/137530 A1 | 9/2014 |
| WO | WO 2015/049391 A1 | 4/2015 |
| WO | WO 2017/132004 A1 | 8/2017 |
| WO | WO 2020/040649 A1 | 2/2020 |

OTHER PUBLICATIONS

International Search Report and Written Opinion dated Aug. 3, 2021, for International Application No. PCT/EP2021/061428, 15 pages.
International Search Report and Written Opinion dated Jul. 16, 2021, for International Application No. PCT/EP2021/061442, 13 pages.
International Search Report and Written Opinion dated Jul. 8, 2021, for International Application No. PCT/EP2021/061447, 15 pages.
International Search Report and Written Opinion dated Jul. 27, 2021, for International Application No. PCT/EP2021/061456, 14 pages.
International Search Report and Written Opinion dated Jul. 13, 2021, for International Application No. PCT/EP2021/061459, 16 pages.
International Search Report and Written Opinion dated Jul. 20, 2021, for International Application No. PCT/EP2021/061466, 17 pages.
International Search Report and Written Opinion dated Jul. 15, 2021, for International Application No. PCT/EP2021/061468, 16 pages.

* cited by examiner

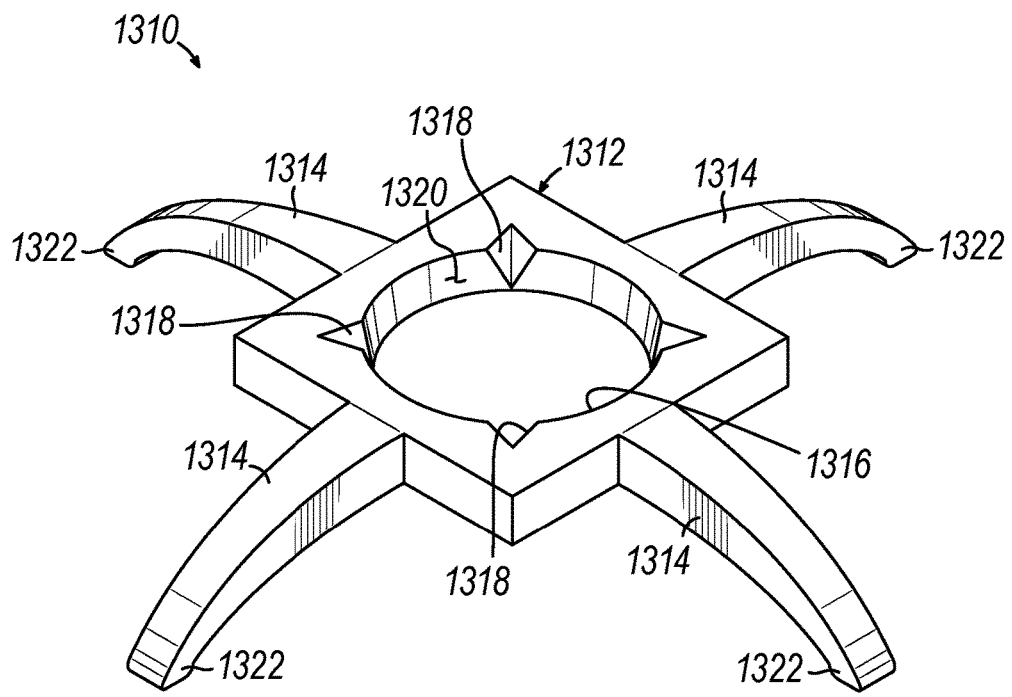
FIG. 17
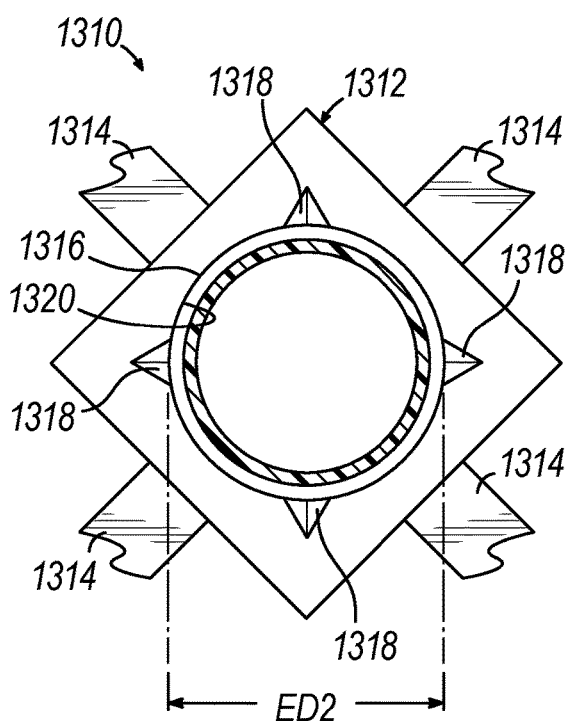 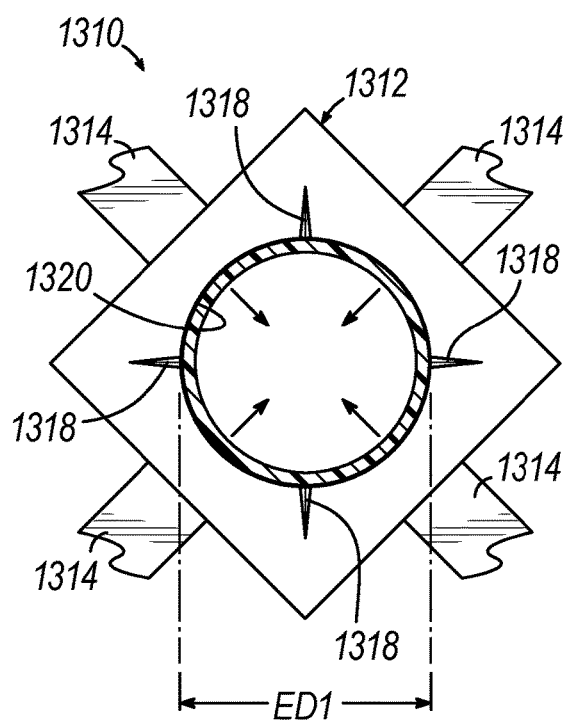
FIG. 18A      FIG. 18B

TILTING TANG CANNULA DEPTH LIMITER

PRIORITY

This application claims the benefit of U.S. Provisional Pat. App. No. 63/018,652 entitled "Tilting Tang Cannula Depth Limiter," filed on May 1, 2020.

BACKGROUND

Some surgical procedures may require a clinician to access a surgical site via the abdominal cavity of a patient. To gain such access, an opening is first formed through the abdominal wall tissue overlying the abdominal cavity. In some surgical procedures (referred to as "laparoscopic" or "endoscopic" surgeries), a relatively small opening is made through the abdominal wall tissue, and the surgical site is then accessed with elongate instruments inserted through an access device generally referred to as a "trocar" positioned within the opening. Traditional trocars generally include a cannula assembly and an obturator that is removably received within a working channel of the cannula assembly. In use, the obturator is mated with the cannula assembly, and the combined structure (i.e., the trocar) is directed by a clinician downwardly through the abdominal wall of the patient such that the distal ends of the obturator and the cannula assembly extend into the abdominal cavity. The clinician then withdraws the obturator from the cannula assembly so that surgical instruments may be directed downwardly through the working channel of the cannula assembly to access the surgical site.

Merely exemplary versions of trocars, components thereof, and other varieties of surgical access devices are disclosed in U.S. Pat. No. 7,981,092, entitled "Vibratory Trocar," issued Jul. 19, 2011; U.S. Pat. No. 8,226,553, entitled "Access Device with Insert," issued on Jul. 24, 2012; U.S. Pat. No. 8,251,900, entitled "Surgical Access Devices and Methods Providing Seal Movement in Pre-defined Paths," issued on Aug. 28, 2012; U.S. Pat. No. 8,579,807, entitled "Absorbing Fluids in a Surgical Access Device," issued on Nov. 12, 2013; U.S. Pat. No. 8,568,362, entitled "Surgical Access Device with Sorbents," issued on Oct. 29, 2013; U.S. Pat. No. 8,636,686, entitled "Surgical Access Device," issued on Jan. 28, 2014; U.S. Pat. No. 8,690,831, entitled "Gas Jet Fluid Removal in a Trocar," issued on Apr. 8, 2014; and U.S. Pat. Pub. No. 2019/0000496, entitled "Method of Suturing a Trocar Path Incision," published Jan. 3, 2019, issued as U.S. Pat. No. 11,389,192 on Jul. 19, 2022. The disclosure of each of the above-cited U.S. Patents and Publications is incorporated by reference herein.

In some procedures, it may be desirable to limit the depth that the trocar mentioned above is inserted into the body cavity wall of the patient. It may be further desirable to have one depth limiter that is reusable and may be used with both reusable and disposable trocars. While various kinds of surgical instruments, including surgical access devices and end effectors, and other associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 17 depicts a perspective view of a seventh exemplary depth limiter that includes a hub with notches;

FIG. 18A depicts a top plan view of the depth limiter of FIG. 17 coupled with the cannula tube of the cannula assembly of FIG. 5, where the hub of the depth limiter is in a movable configuration;

FIG. 18B depicts a partial side sectional view of the depth limiter of FIG. 17 coupled with the cannula tube of the cannula assembly of FIG. 5 following detachment and removal of the obturator, where the legs of the depth limiter are in a fixed configuration;

Figure 1:
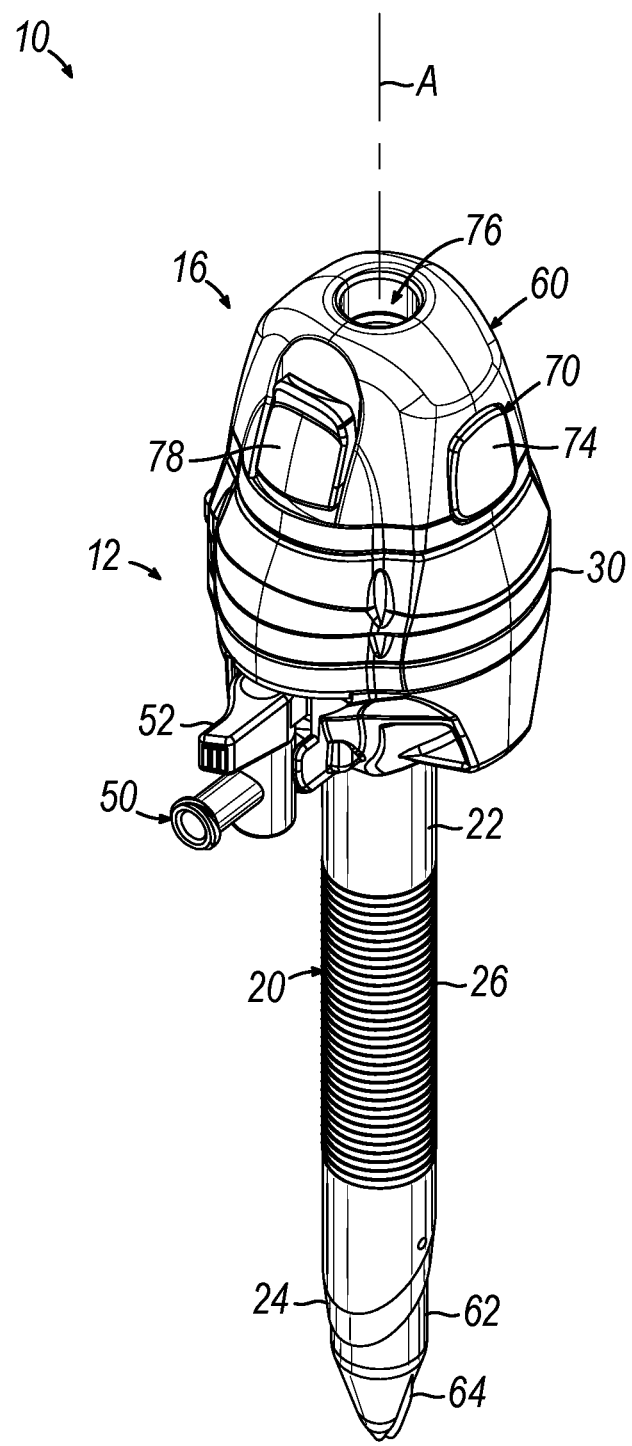
FIG. 1 depicts a perspective view of an exemplary trocar having a cannula assembly and an obturator shown in an assembled state.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical device. The term "proximal" refers to the position of an element arranged closer to the surgeon, and the term "distal" refers to the position of an element arranged further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

Furthermore, the terms "about," "approximately," and the like as used herein in connection with any numerical values or ranges of values are intended to encompass the exact value(s) referenced as well as a suitable tolerance that enables the referenced feature or combination of features to function for the intended purpose(s) described herein.

I. Exemplary Single-Use and Reusable Trocars

FIGS. 1-5 depict exemplary surgical access devices in the form of a single-use first trocar (10) and a reusable second trocar (110), each configured to provide surgical site access in a laparoscopic surgical procedure. Each trocar (10, 110) includes a cannula assembly (12, 112) having a working channel (14, 114), and an obturator (16, 116) configured to be removably inserted coaxially into the working channel (14, 114) so that the assembled trocar (10, 110) may be directed distally through the abdominal wall of a patient and into the abdominal cavity, for example as described below in connection with FIGS. 3A-3D.

A. Exemplary Single-Use Trocar

Figure 2:
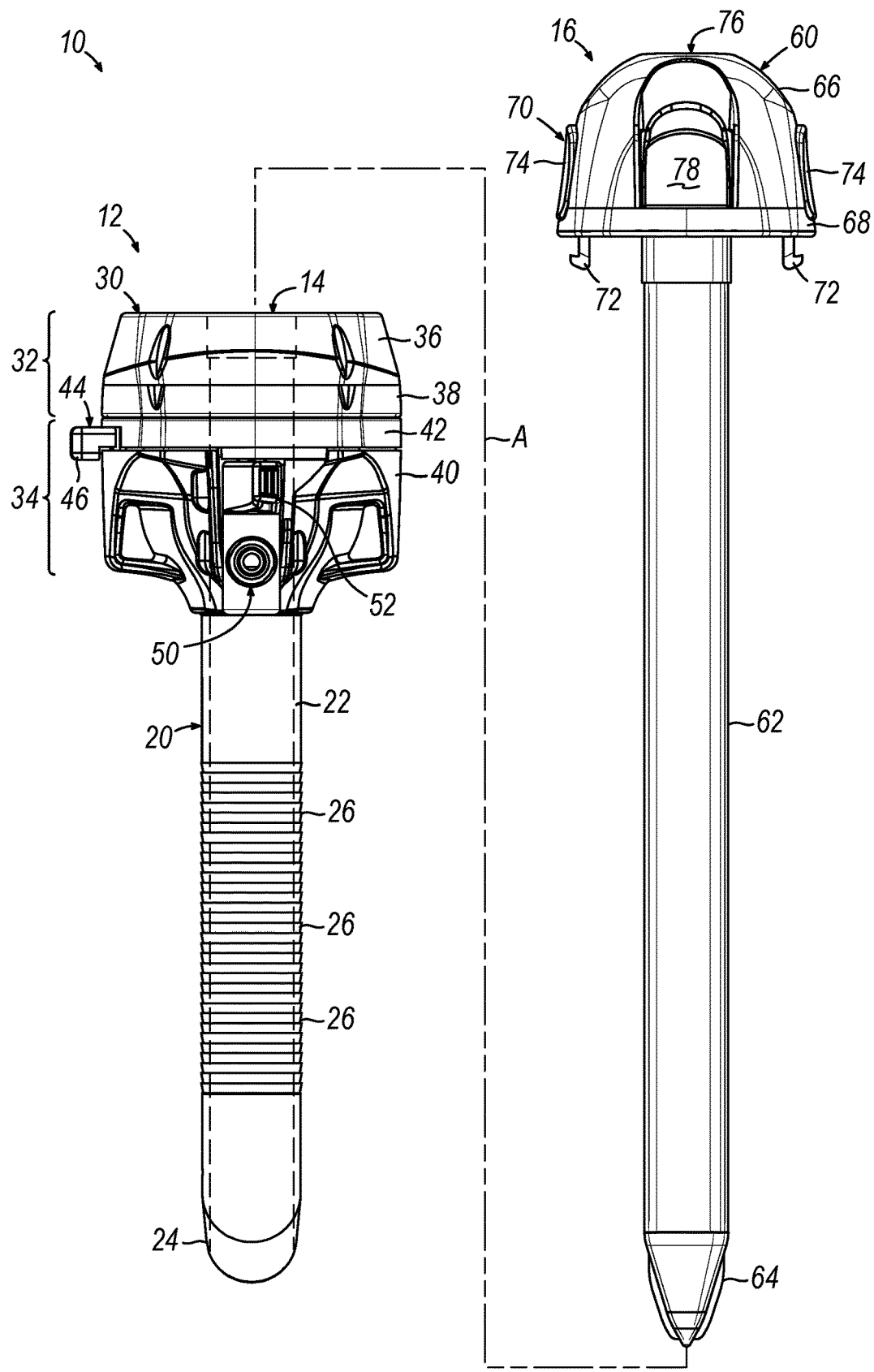
FIG. 2 depicts a side elevational view of the cannula assembly and the obturator of FIG. 1 in a disassembled state.

As shown in FIGS. 1-2, cannula assembly (12) of single-use trocar (10) includes a cannula (20) and a seal housing (30). Cannula (20) and seal housing (30) cooperate to define working channel (14), which extends longitudinally along a central axis (A) of trocar (10). In particular, working channel (14) is defined by a lumen of cannula (20) in communication with a hollow interior of seal housing (30). Cannula assembly (12) is configured to receive elongate surgical instruments distally through working channel (14) to provide access to surgical sites within the abdominal cavity of a patient. As described in greater detail below, seal housing (30) houses a pair of seal structures defining a seal assembly configured to maintain insufflation of the patient's abdominal cavity while permitting passage of surgical instruments and tissue fragments along working channel (14).

Cannula (20) of the present version may include a bell-shaped hub (not shown) at a proximal end thereof, and an elongate cylindrical cannula tube (22) extending distally from the hub and terminating at an angled cannula tip (24). An outer surface of cannula tube (22) includes a plurality of tissue gripping features in the form of annular ribs (26) arranged axially along a medial portion of cannula tube (22). Ribs (26) are configured to grip the layers of abdominal wall tissue through which cannula (20) is inserted, and thereby assist in stabilizing cannula (20) in axial and radial directions while cannula (20) is positioned within the opening formed in the abdominal wall of a patient.

More specifically, tissue gripping ribs (26) of the present example are formed as annular scallops in the sidewall of cannula tube (22) such that each rib (26) tapers radially inwardly in a distal direction from a radially outermost edge of the rib (26). The radially outermost edges of ribs (26) are thus generally flush with the non-ribbed proximal and distal portions of cannula tube (22). The resulting configuration of ribs (26) promotes advancement of cannula tube (22) through tissue layers in a distal direction and resists retraction of cannula tube (22) through the tissue layers in a reverse, proximal direction. Advantageously, this configuration protects against unintended withdrawal of cannula tube (22) from the abdominal wall of patient during a surgical procedure. It will be appreciated, however, that cannula tube (22) may be provided with various other types of tissue gripping features in other versions of trocar (10). For instance, cannula tube (22) may include a tissue gripping feature in the form of one or more helical ribs that extend around at least a medial portion of cannula tube (22), and which may be scalloped similar to ribs (26).

Seal housing (30) of cannula assembly (12) includes a proximal housing portion (32) and a distal housing portion (34) to which proximal housing portion (32) is removably attached. Proximal housing portion (32) includes a seal housing head (36) and a distal base (38) secured together. Distal housing portion (34) includes a distal shroud (40) that encircles the proximal hub (not shown) of cannula (20), a cap plate (42) secured to a proximal end of distal shroud (40), and a latch ring (44) rotatably disposed therebetween and having a radially outwardly projecting tab (46). Latch ring (44) is selectively rotatable via tab (46) about the central axis (A) of trocar (10) between a locked position and an unlocked position. In the locked position, latch ring (44) locks proximal housing portion (32) to distal housing portion (34). In the unlocked position, latch ring (44) permits separation of proximal housing portion (32) from distal housing portion (34), for example to directly access a distal seal structure (not shown) housed within distal housing portion (34). In some versions, distal shroud (40) may be formed integrally with the proximal end of cannula tube (22) such that distal shroud (40) is a component of cannula (20).

Though not shown, proximal housing portion (32) houses a proximal (or "outer") seal structure, and distal housing portion (34) houses a distal (or "inner") seal structure, both arranged along the central axis (A) of trocar (10). The proximal and distal seal structures cooperate to define a seal assembly that maintains insufflation of the patient's abdominal cavity during a surgical procedure while permitting passage of surgical instruments and tissue fragments along working channel (14). For instance, the proximal seal structure may include an annular seal member configured to sealingly engage the shaft of a laparoscopic surgical instrument directed through working channel (14). The distal seal structure may include a duckbill seal member configured to maintain working channel (14) in a sealed stated in the absence of a surgical instrument shaft.

Cannula assembly (12) further includes an insufflation port (50) operatively coupled with the proximal end of cannula (20) and having an adjustable valve in the form of a stopcock (52). Insufflation port (50) is configured to direct insufflation fluid, such as carbon dioxide, from a fluid source (not shown) distally through working channel (14) and into the patient's abdominal cavity to thereby expand (or "insufflate") the cavity with the fluid. This expansion of the abdominal cavity creates additional space for performing a laparoscopic surgical procedure with improved ease.

As shown in FIGS. 1 and 2, obturator (16) of trocar (10) includes an obturator head (60), an elongate cylindrical obturator shaft (62) extending distally from head (60), and a tapered distal obturator tip (64). Obturator shaft (62) is configured to be received within working channel (14) of cannula assembly (12) such that obturator tip (64) extends through and distally of cannula tip (24). Obturator head (60) includes a domed upper body (66), a base plate (68), and an actuatable latch member (70), which includes a pair of latch arms (72) and a corresponding pair of latch buttons (74). Latch arms (72) are configured to be captured within respective slots (not shown) formed in a top surface of seal housing head (36) to couple obturator (16) with cannula assembly (12). Latch buttons (74) are actuatable to release latch arms (72) from the slots and thereby permit separation of obturator (16) from cannula assembly (12). Obturator (16) further includes a central passage (76) that extends longitudinally through obturator head (60) and obturator shaft (62), and is configured to receive an endoscope (not shown) therein to provide visualization during insertion of trocar (10) through the abdominal wall of a patient. A clamp lever (78) of obturator head (60) is pivotable to selectively fix the endoscope within central passage (76). Central passage (76) and clamp lever (78) are merely optional features and may be omitted from obturator (16) in other versions.

Cannula assembly (12) and obturator (16) may be constructed to be disposed of after a single use with a patient. In other versions, one or more components of trocar (10) may be suitably constructed to withstand sterilization and multiple reuses, for example as described in greater detail below in connection with trocar (110) of FIGS. 4-5.

B. Exemplary Deployment of Trocar into Patient Abdominal Cavity

FIGS. 3A-3D illustrate an exemplary method of accessing an abdominal cavity (1) of a patient through the patient's abdominal wall (2) with trocar (10) described above. It will be appreciated that abdominal wall (2) includes outward superficial layers and inward deep layers. Superficial layers generally include an outer layer of skin (3) and an inner layer of fat (4); whereas the deeper layers include alternating layers of muscle (5) and fascia (6), which are fibrous and flexible with relatively higher tensile strength than the superficial layers.

Figure 3A:
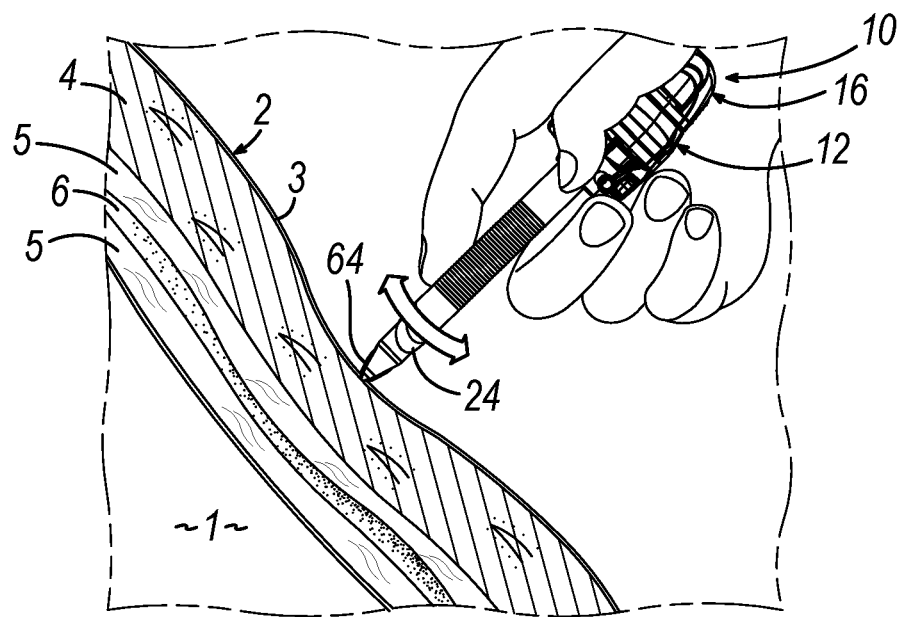
FIG. 3A depicts a side sectional view of the trocar of FIG. 1 being manipulated by a clinician through tissue layers of an abdominal wall.
Figure 3B:
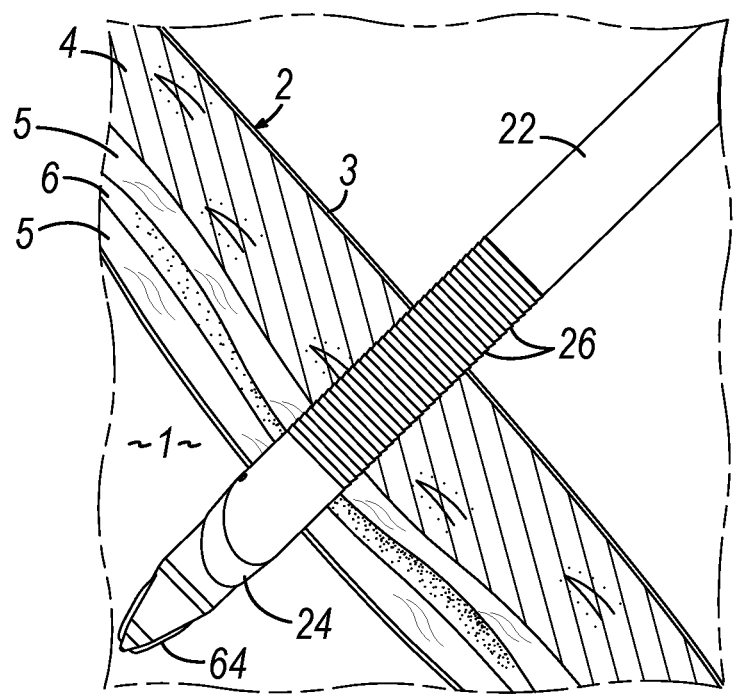
FIG. 3B depicts an enlarged side sectional view of the trocar of FIG. 1, showing a distal end of the trocar received within the abdominal cavity of FIG. 3A.
Figure 3C:
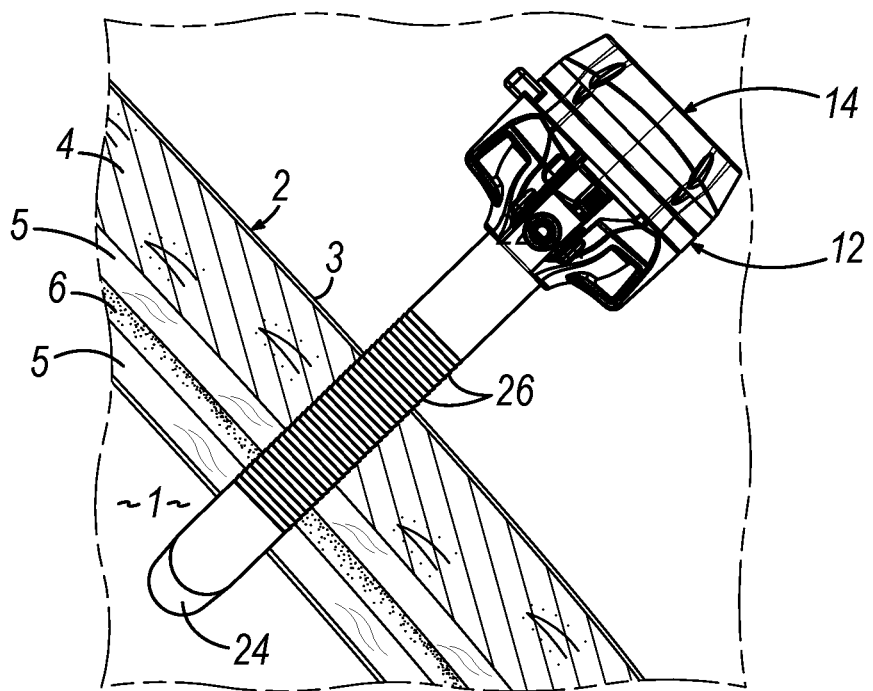
FIG. 3C depicts a side sectional view of the cannula assembly of FIG. 1, showing the cannula assembly remaining positioned within the abdominal wall of FIG. 3A following detachment and removal of the obturator.
Figure 3D:
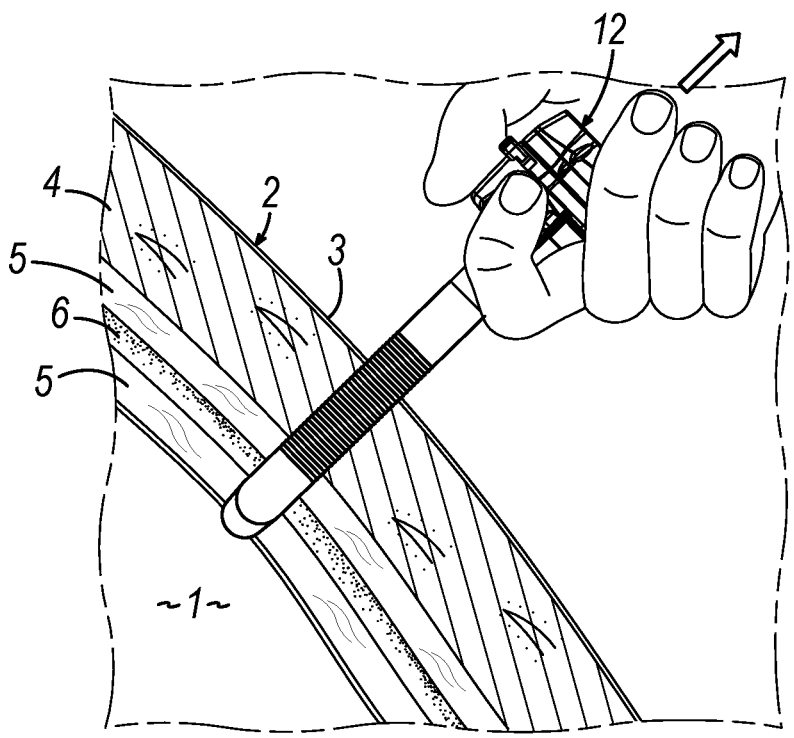
FIG. 3D depicts a side sectional view of the cannula assembly of FIG. 1 being withdrawn proximally from the abdominal wall of FIG. 3A.

As shown in FIG. 3A, with obturator (16) received within cannula assembly (12) and connected to seal housing (30), a clinician manipulates trocar (10) via obturator head (60) and seal housing (30) to urge obturator tip (64) against skin (3) and inward toward abdominal cavity (1) while rotating trocar (10) back and forth. Continued inward urging of trocar (10) further directs obturator tip (64) and cannula tip (24) distally through the layers of fat (4) and fascia (6) and into cavity (1), as shown in FIG. 3B. As discussed above, this step may be facilitated with visualization provided by an endoscope (not shown) mounted within obturator (16). Once cannula (20) has reached a desired depth of insertion into cavity (1), the clinician releases obturator head (60) from seal housing (30) via depression of latch buttons (74), and then withdraws obturator (16) from proximally from cannula assembly (12), as shown in FIG. 3C. This renders working channel (14) of cannula assembly (12) free to receive surgical instruments distally therethrough for performing the laparoscopic surgical procedure. As described above, tissue gripping ribs (26) provided on cannula tube (22) grip the layers of tissue (3, 4, 5, 6) of abdominal wall (2), thus providing cannula assembly (12) with at least a minimum degree of stability relative to abdominal wall (2). Upon completion of the laparoscopic surgical procedure, the clinician grasps seal housing (30) and withdraws cannula assembly (12) proximally from abdominal wall (2), as shown in FIG. 3D.

C. Exemplary Reusable Trocar Having Disposable Seal Assembly

Figure 4:
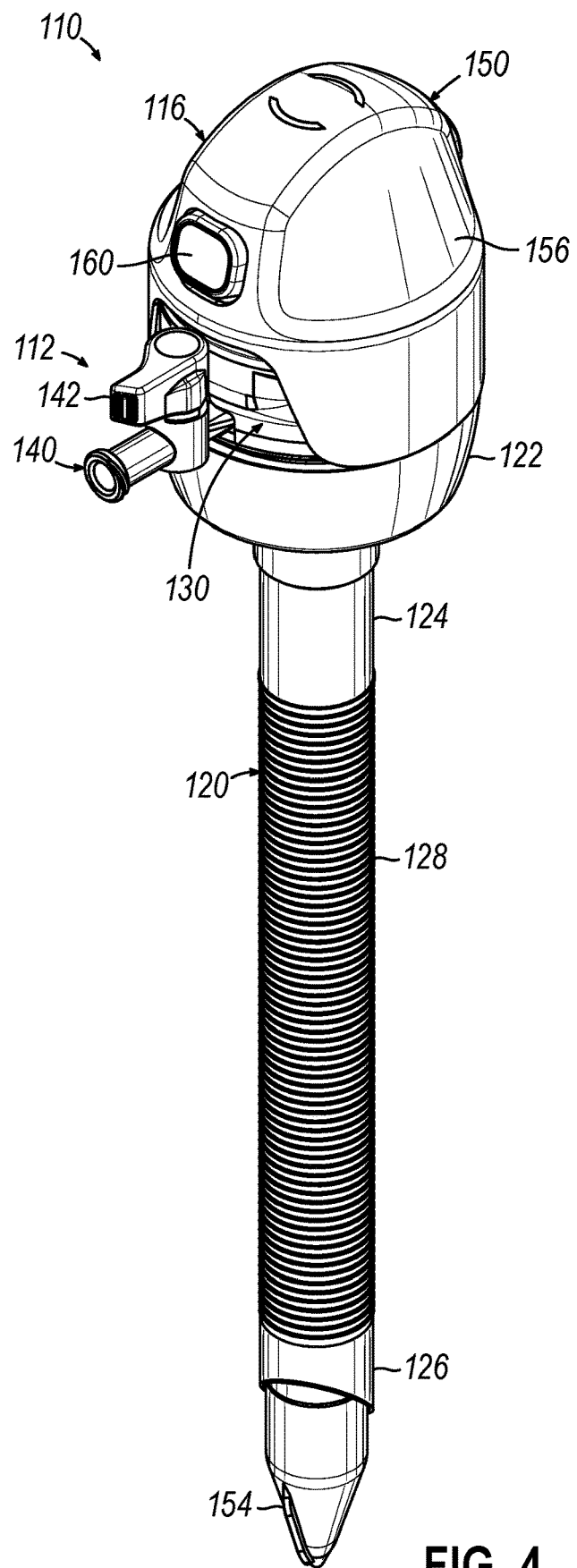
FIG. 4 depicts a perspective view of another exemplary trocar having a cannula assembly and an obturator shown in an assembled state.
Figure 5:
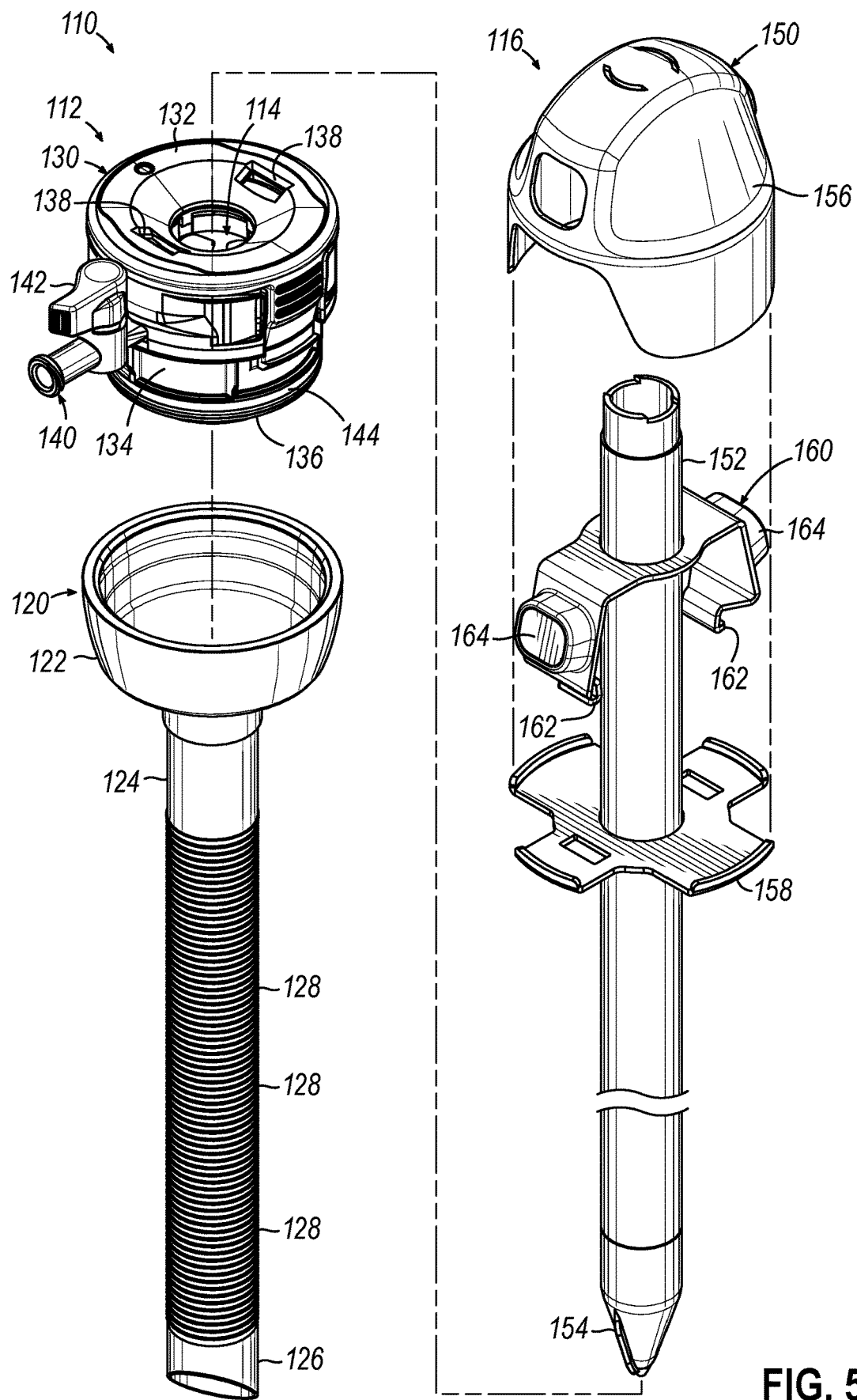
FIG. 5 depicts a perspective view of the cannula assembly and the obturator of FIG. 4 in a disassembled state, showing a reusable cannula and a disposable seal assembly of the cannula assembly separated from one another, and showing the obturator in an exploded state.

In some instances, it may be desirable to configure a trocar such that one or more components thereof may be sterilized and reused for multiple surgical procedures, while one or more other components may be easily and economically disposed of and replaced after each procedure. FIGS. 4-5 show another exemplary trocar (110) that is configured in such a manner, and which is similar in structure and function to trocar (10) described above except as otherwise described below.

Similar to trocar (10), trocar (110) includes a cannula assembly (112) having a working channel (114) and an obturator (116) configured to be inserted into cannula assembly (112) coaxially along working channel (114). Cannula assembly (112) includes a cannula (120) having a bell-shaped proximal hub (122) at a proximal end thereof, and an elongate cylindrical cannula tube (124) extending distally from proximal hub (122) and terminating at an angled cannula tip (126). An outer surface of cannula tube (124) includes a plurality of tissue gripping features in the form of annular ribs (128) arranged axially along a medial portion of cannula tube (124) and which are similar to ribs (26) described above.

Cannula assembly (112) further includes a seal assembly (130). Unlike the seal assembly defined by seal housing (30) of trocar (10), seal assembly (130) is constructed as a modular, replaceable unit configured to releasably mate with proximal hub (122) of cannula (120). As shown best in FIG. 5, seal assembly (130) of the present example generally includes an upper frame member (132), a middle frame member (134), and a lower frame member (136) secured relative to one another in a coaxial arrangement. Though not shown, a proximal (or "outer") seal structure is supported within upper frame member (132), and a distal (or "inner") seal structure is supported within lower frame member (136). Such seal structures may be similar in structure and function to the proximal and distal seal structures of trocar (10) described above. Seal assembly (130) further includes an insufflation port (140) having an adjustable valve in the form of a stopcock (142).

A lower portion of seal assembly (130) distal to insufflation port (140) is configured to seat within proximal hub (122) of cannula (120) such than an annular seal member (144) disposed circumferentially about the lower portion sealingly engages an inner surface of proximal hub (122). In this manner, an interior of seal assembly (130) fluidly communicates with a lumen of cannula (120) to define a working channel (114) of cannula assembly (112) through which insufflation fluid, surgical instruments, and tissue fragments may be directed in the manners generally described above in connection with trocar (10). Seal assembly (130) may be further configured in accordance with one or more teachings of U.S. Pat. Pub. No. 2019/0090905, entitled "Trocar Seal Assemblies," published Mar. 28, 2019, issued as U.S. Pat. No. 10,792,069 on Oct. 6, 2020, the disclosure of which is incorporated by reference herein; and/or U.S. Pat. Pub. No. 2019/0380742, entitled "Asymmetric Shaft Seal," published Dec. 19, 2019, issued as U.S. Pat. No. 10,820,924 on Nov. 3, 2020, the disclosure of which is incorporated by reference herein.

As shown best in FIG. 5, obturator (116) of trocar (110) includes a proximal obturator head (150), an elongate cylindrical shaft (152) extending distally from obturator head (150), and a tapered tip (154) at a distal end of shaft (152). Obturator head (150) includes a domed upper body (156), a base plate (158), and an actuatable latch member (160), which includes a pair of downwardly extending latch arms (162) and a corresponding pair of latch buttons (164). Latch arms (162) are configured to be captured within respective slots (138) formed in a top surface of upper frame member (132) of seal assembly (130) to couple obturator (116) with cannula assembly (112). Latch buttons (164) are actuatable to release latch arms (162) from slots (138) and thereby permit separation of obturator (116) from cannula assembly (112).

Cannula (120) and obturator (116) of the present example are suitably constructed of a robust material, such as surgical steel, such that they may be sterilized and reused for multiple surgical procedures. In contrast, as described above, seal assembly (130) is constructed as a disposable unit, intended to be separated from cannula (120) and replaced after each procedure. For instance, seal assembly (130) may be constructed of various polymeric materials, including plastics and rubbers, such that seal assembly (130) may be easily manufactured and sold at a price point that renders seal assembly (130) suitable for disposal after a single use, similar to trocar (10) described above.

II. Exemplary Cannula Depth Limiters

In some scenarios, a clinician may wish to limit the depth to which a single-use or reusable trocar (10, 110) may travel into abdominal wall (2) (e.g., after insertion of trocar (10, 110) to a desired position). Limiting the depth to which trocar (10,110) may travel into abdominal wall (2) may assist in preventing distal obturator tip (64) from inadvertently entering deeper than desired into abdominal cavity (1). Preventing over insertion of trocar (10, 110) may also avoid inadvertently reducing the available working space within the abdominal cavity (1).

Alternatively, or in addition, the clinician may desire to stabilize the trocar (10, 110) relative to abdominal wall (2) (e.g., after insertion of trocar (10, 110) to a desired position in abdominal cavity (1)). The clinician may stabilize trocar (10, 110) relative to abdominal wall (2) by avoiding under insertion of trocar (10, 110). Stabilizing trocar (10, 110) relative to abdominal wall (2) after insertion into abdominal wall (2) may assist in preventing trocar (10, 110) from inadvertently pivoting about the insertion point in abdominal wall (2) after the clinician releases trocar (10, 110). Stabilizing trocar (10, 110) maintains cannula tube (22, 124), and thus the entry point of surgical instruments into abdominal cavity (1) in a desired position and/or orientation relative to abdominal cavity (1) such that surgical instruments may be easily directed distally through trocar (10, 110) at a selected working angle that is convenient to the clinician. It may also be desirable to design a reusable depth limiting device that has a limited number of voids and recesses. This design will simplify the manufacturing process and aid in sanitizing and cleaning the surgical instrument.

A. First Exemplary Depth Limiter Having Spring Latch Arm

Figure 6:
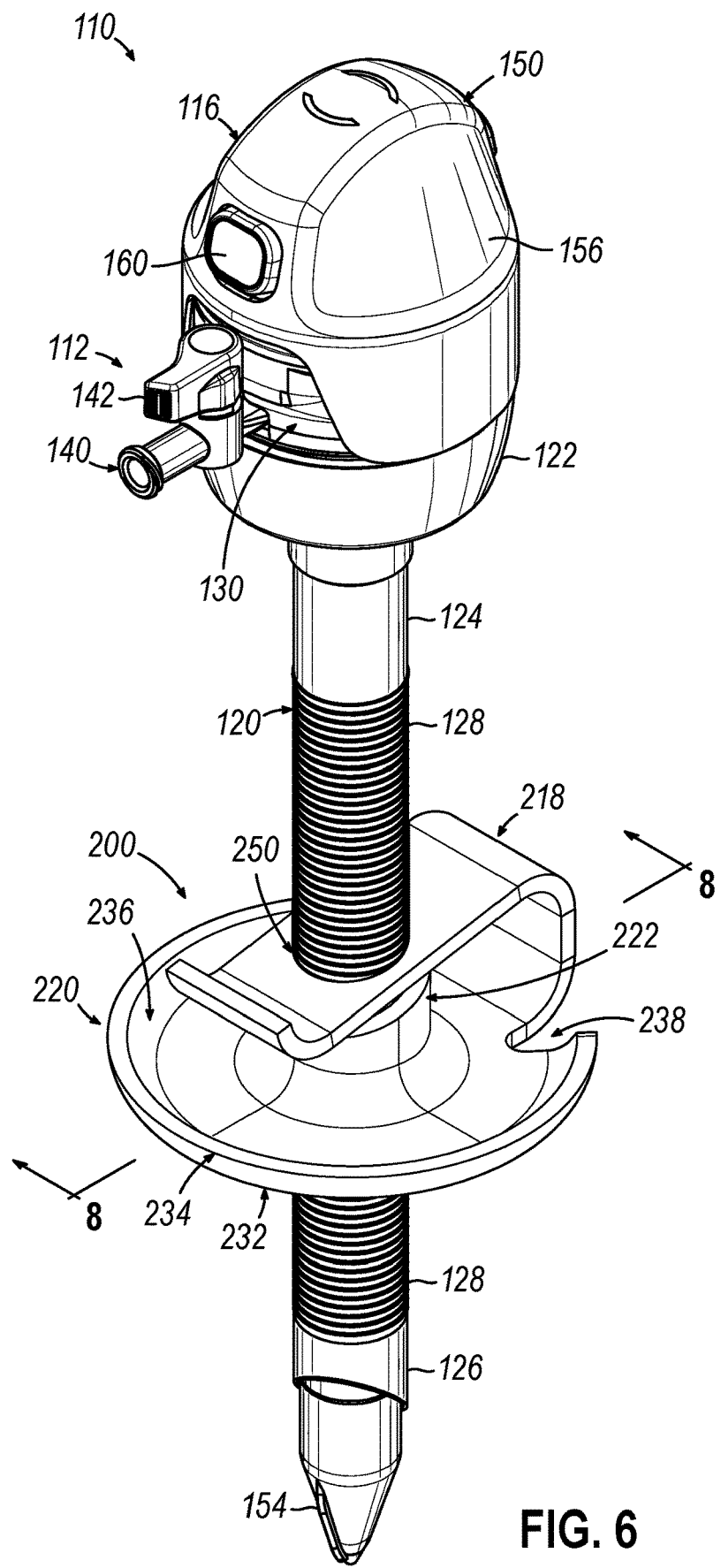
FIG. 6 depicts a perspective view of an exemplary depth limiter coupled to a cannula tube of the cannula assembly of FIG. 4, showing a latch arm of the depth limiter in an initial lock position that inhibits relative translation between the depth limiter and the cannula tube.

FIG. 6 shows an example of a depth limiter (200) coupled to cannula tube (124) of trocar (110). Though not shown, it will be appreciated that depth (200) may also be used with trocar (10). As described in greater detail below, depth limiter (200) may selectively limit the depth to which trocar (10, 110) may travel distally into abdominal wall (2).

Figure 7:
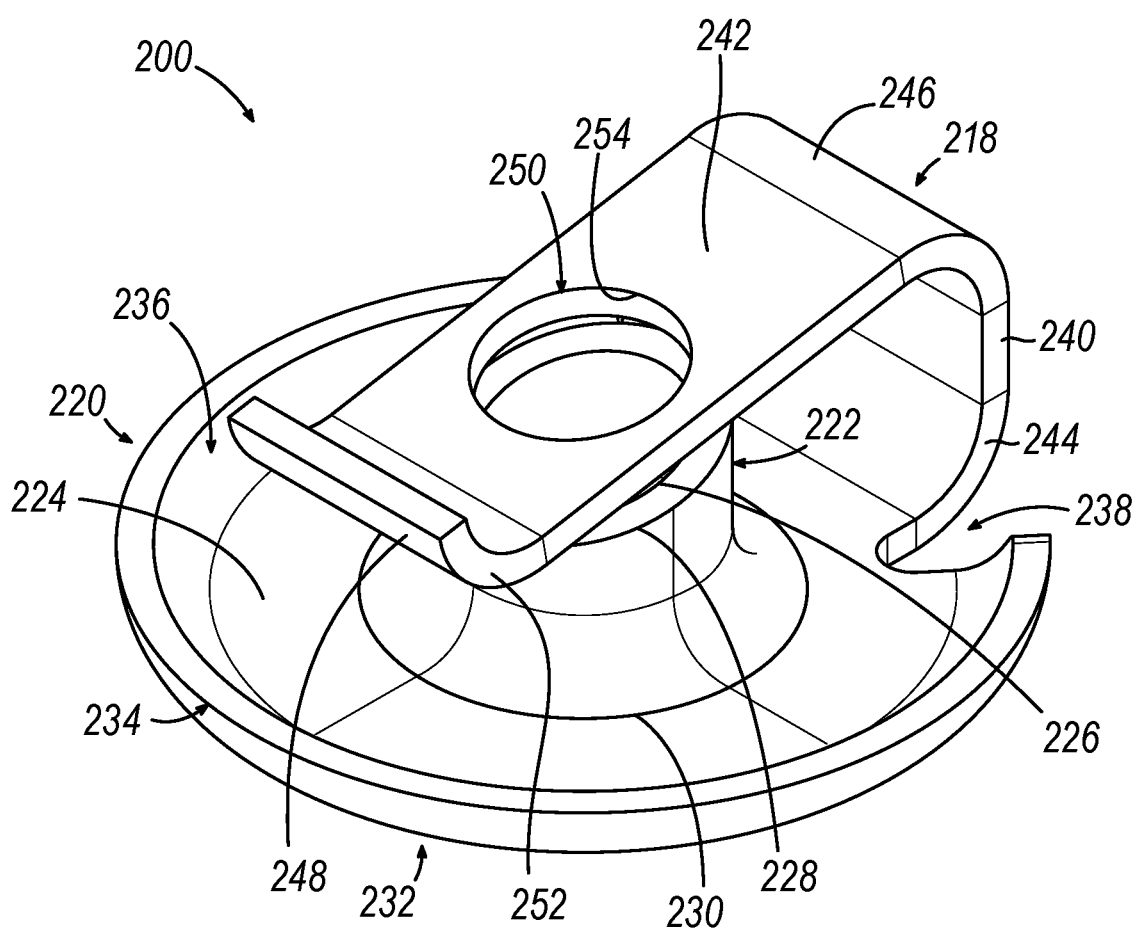
FIG. 7 depicts a perspective view of the depth limiter of FIG. 6, showing the latch arm in the initial lock position.
Figure 8A:
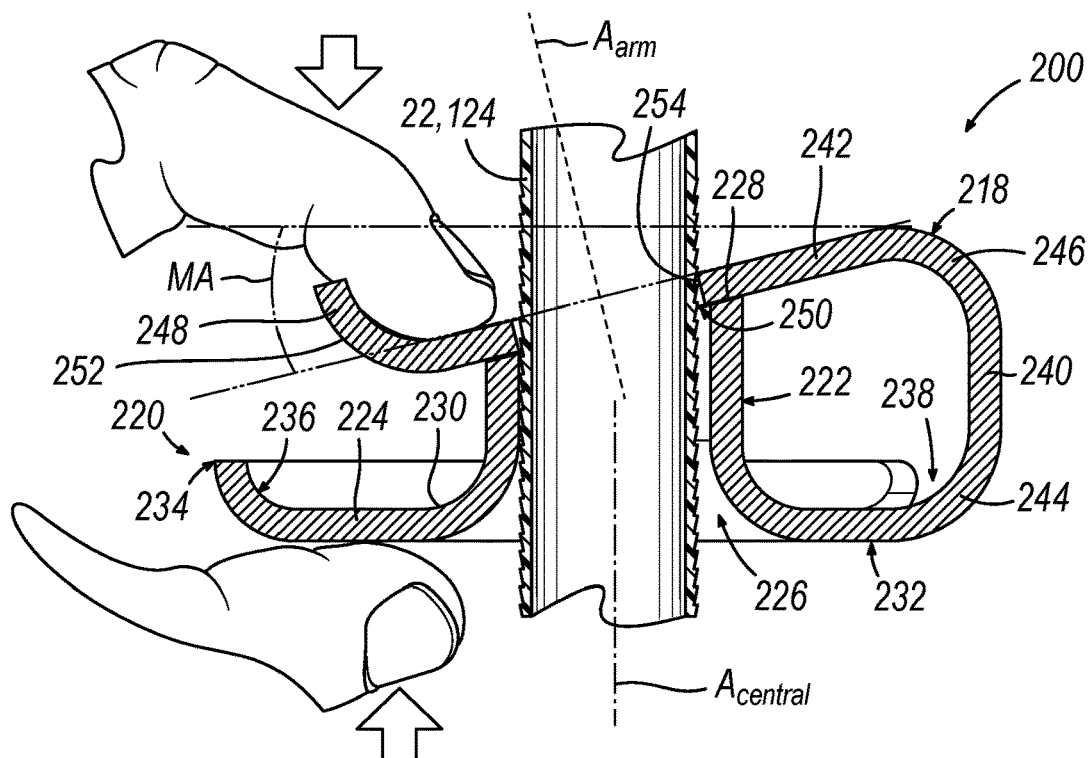
FIG. 8A depicts a side sectional view of the depth limiter and the cannula tube of FIG. 6, showing the latch arm in a fully locked position that inhibits relative translation between the depth limiter and the cannula tube.
Figure 8B:
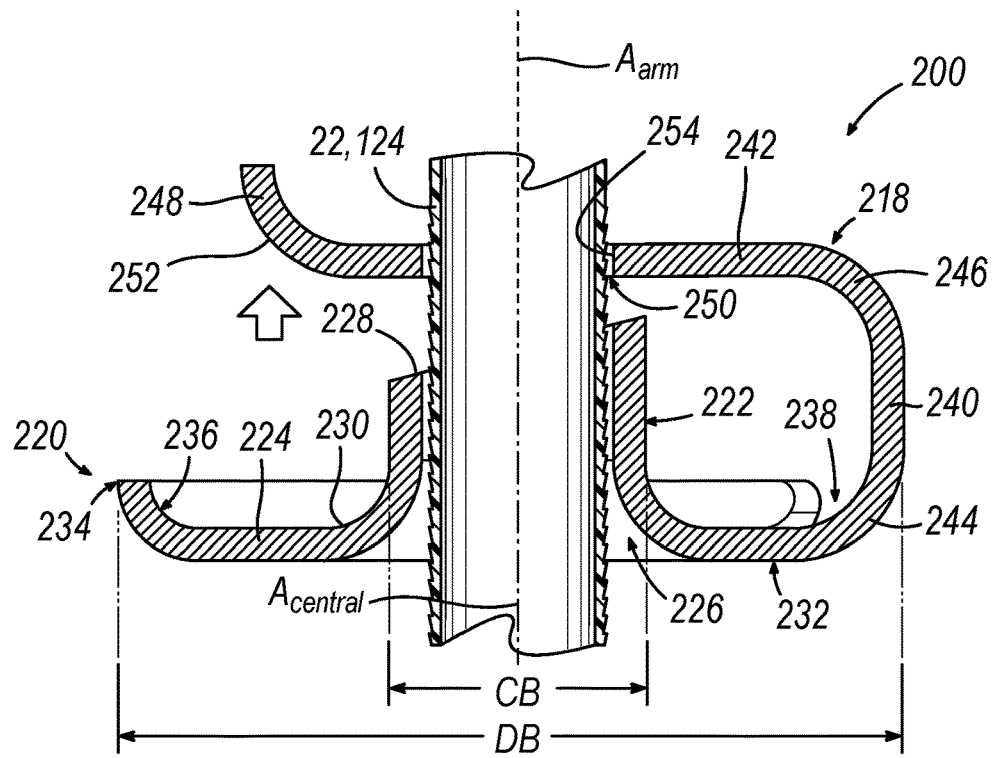
FIG. 8B depicts a side sectional view of the depth limiter and the cannula tube of FIG. 6, showing the latch arm in a release position that permits relative translation between the depth limiter and the cannula tube.

As best shown in FIGS. 7-8B, depth limiter (200) of the present version includes a latch arm (218) integrally coupled to an annular base (220). The annular base (220) is relatively rigid relative to the latch arm (218), which is flexible and has resilient properties. In particular, latch arm (218) is in the form of a spring arm that is resiliently deflectable relative to base (220) between an initial lock position shown in FIGS. 6-7, a full lock position shown in FIG. 8A, and a release position shown in FIG. 8B.

In each of the initial and full locked positions, latch arm (218) is configured to frictionally engage an outer surface of cannula tube (124) (e.g., annular ribs (128)) and thereby inhibit relative translation between depth limiter (200) and cannula tube (124). In contrast, latch arm (218) in the release position is configured to permit relative translation between depth limiter (200) and cannula tube (124). As described below, the full lock position provides a greater degree of frictional engagement between latch arm (218) and cannula tube (124) than the initial lock position, thus providing a greater resistance to relative axial loads exerted between depth limiter (200) and cannula tube (124). Latch arm (218) of the present example is resiliently biased toward the initial lock position such that latch arm (218) may be deflected by a user downwardly toward base (220) (i.e., distally) to the full lock position, or upwardly away from base (220) (i.e., proximally) to the release position.

Depth limiter (200) may be constructed of any one or more suitable materials. For instance, depth limiter (200) may be constructed of a surgically safe metal, such as surgical stainless steel, or alternatively a polymetric material. It will be understood that a construction of metal would render depth limiter (200) sterilizable, making it reusable for multiple surgical procedures. By comparison, a construction of plastic may render depth limiter (200) suitable for disposal after a single use, similar to trocar (10) and seal assembly (130) described above. In the present example, annular base (220) and latch arm (218) are formed together as a unitary piece. This unitary piece may be formed by one or more suitable manufacturing processes, such as metal stamping, additive manufacturing, die casting, or injection molding, for example. In other versions of depth limiter (200), one or more components may be formed separately and then coupled together.

In the present example shown, annular base (220) includes a cylindrical central boss (222) and an annular hub (224) extending radially outwardly from and circumferentially about central boss (222). Central boss (222) includes a boss lumen (226) and extends distally along a central axis ($A_{central}$) of base (220) from a proximal face (228) to an outwardly flared distal portion (230), which may be non-flared in other versions. Proximal face (228) is obliquely positioned relative to central axis ($A_{central}$) and acts as a stop for latch arm (218) in the full locked position, as shown in FIG. 8A. In particular, proximal face (228) restricts latch arm (218) from being deflected distally beyond a maximum deflection angle (MA), thereby preventing unwanted plastic deformation of latch arm (218) and/or excessive frictional engagement of and resulting damage to cannula tube (124) or latch arm (218). It will be appreciated that an axial height of central boss (222) and the angle of proximal face (228) may be selected to permit a predetermined maximum deflection angle (MA) of latch arm (218) and/or a predetermined degree of frictional engagement with cannula tube (124), which criteria may be selected based at least in part on the material composition of depth limiter (200) and/or cannula tube (124). Boss lumen (226) is sized to slidably receive cannula tube (22, 124) of cannula assembly (12, 112). Annular hub (224) radially extends outwardly from distal portion (230) of central boss (222) towards an outer edge (234), which may be rolled proximally as shown in order to ensure an atraumatic interaction with the abdominal wall (2) of the patient.

Annular base (220) as shown in the present version has a generally circular shape, but annular base (220) may be formed with various other shapes in other versions, such as oval, rectangular, or triangular, for example. Annular hub (224) has an underside (232) that is generally planar and has a base diameter (DB) that is larger than a central boss diameter (CB). Base diameter (DB) suitably sized to prevent depth limiter (200) from passing distally through a trocar path incision in the abdominal wall (2) of the patient. Underside (232) may be smooth as shown or constructed with a texture (not shown) or another surface effect (not shown) to further assist in maintaining cannula tube (22, 124) upright within the abdominal wall (2).

In the example shown, outer edge (234) of annular base (220) is located radially outwardly from central boss (222) and is curled (or "rolled") proximally away from the skin of a patient and toward latch arm (218). Outer edge (234) may thus increase the rigidity of annular base (220) and provide a smooth contour for comfort to the patient. Additionally, curve portion (236) of outer edge (234) may act as a user gripping feature so that a clinician may more readily grasp outer edge (234). Outer edge (234) includes a pair of relief cut features (238) located on both sides of a first bend (244) of latch arm (218). Relief cut features (238) promote resilient deflection of first bend (244) of latch arm (218) relative to base (220). Relief cut features (238) enable latch arm (218) to have additional flexibility because latch arm (218) is not abutted with an outer edge (234) that adds rigidity to latch arm (218).

As shown in FIG. 7, latch arm (218) includes a first arm portion (240) and a second arm portion (242). First arm portion (240) attaches to annular base (220) at a first bend (244) between pair of relief cut features (238). First bend (244) is generally parallel to central axis ($A_{central}$) and perpendicular to a plane defined by annular base (220). First arm portion (240) extends proximally away from first bend (244) to a second bend (246).

Second bend (246) joins first arm portion (240) second arm portion (242), which extends generally perpendicularly relative to first arm portion (240). Specifically, second arm portion (242) extends radially inwardly towards central axis ($A_{central}$) to a free end (248) having a tang (252) that curves proximally away from base (220) and may be grasped by a used to deflect latch arm (218) relative to base (220). As shown, second arm portion (242) overlies proximal face (228) of central boss (222) and includes an arm opening (250) configured to align coaxially with boss lumen (226) in the release position of latch arm (218).

In the present example, arm opening (250) has the same cross-sectional shape as boss lumen (226) and cannula tube (22, 124). As shown, both boss lumen (226) and arm opening (250) have a circular transverse cross-sectional shape in the present version. In some other versions, boss lumen (226) and arm opening (250) may have different transverse cross-sectional shapes.

As shown in FIGS. 8A and 8B, arm opening (250) has an arm axis ($A_{arm}$) that is perpendicular to second arm portion (242) and concentrically located within arm opening (250). Arm opening (250) includes an engagement feature in the form of an inner edge (254) of arm opening (250). Engagement feature facilitates arm opening (250) to frictionally engage ribs (26, 128) of the cannula tube (22, 124) when latch arm (218) is in one of the initial lock position or the full lock position, thereby inhibiting relative longitudinal movement between depth limiter (200) and cannula tube (22, 124). In some instances, this engagement feature may further include geometry that is complementary to ribs (26, 128). For example, the engagement feature may further include a raised portion (not shown) that mates with a recessed portion of ribs (26, 128), and engagement feature may have a recessed portion (not shown) that mates with a raised portion of ribs (26, 128). In some versions, engagement feature may include annular bands (not shown) that mate with ribs (26, 128). In yet other versions, engagement feature may include geometry that is complementary to helical ribs (not shown) formed on cannula tube (22, 124). It will be appreciated that latch arm (218) of the present example in a lock position is also suitably configured to frictionally engage a cannula tube having a smooth outer surface that lacks one or more tissue engagement features (e.g., similar to ribs (26, 128)).

As noted above, latch arm (218) of the present example is resiliently biased away from release position towards the initial lock position. Release position is a proximal position and initial lock position is a distal position. Latch arm (218) may be in the form of a spring arm as shown. In other embodiments, latch arm (218) may be biased towards the initial lock position, or alternatively the full lock position, by an independent biasing member such as a spring (not shown) or another feature apparent to one skilled in the art. In yet other embodiments (not shown), latch arm (218) may be biased towards the release position. Latch arm (218) shown is shown having a flat rectangular cross-sectional profile. In some versions, latch arm (218) may have an arcuate cross-sectional profile, such as a curved rectangular cross-sectional profile. In such versions, latch arm (218) may have an increased rigidity and thus increased resilient bias toward its resting position (e.g., the initial lock position).

FIG. 8A shows latch arm (218) being depressed distally into the full lock position to thereby engage cannula tube (22, 124) with a maximum degree of frictional engagement. As shown in FIG. 8A, when latch arm (218) is in the full locked position the arm opening (250) is non-coaxial relative to boss lumen (226) such that the corresponding axes ($A_{arm}$, $A_{central}$) are angled relative to one another. Additionally, as described above, an underside of second arm portion (242) directly contacts proximal face (228) of central boss (222).

FIG. 8B shows latch arm (218) being lift via tang (252) to actuate latch arm (218) from a lock position (see, e.g., FIGS. 6-8A) proximally away from annular base (220) to the release position. During this transition, latch arm (218) deflects relative to annular base (220) via deflection at and about first bend (244) and/or second bend (246). When arm axis ($A_{arm}$) aligns coaxially with central axis ($A_{central}$), such that arm opening (250) is aligned coaxially with boss lumen (226), latch arm (218) is in the release position (see FIG. 8B). In the release position, second arm portion (242) is generally perpendicular to central axis ($A_{central}$) and thus generally parallel to annular base (220), and depth limiter (200) is free to translate along cannula tube (22, 124).

Once depth limiter (200) is located by the clinician at a desired longitudinal position along cannula tube (22, 124), the clinician may then release tang (252). In response, latch arm (218) resiliently returns toward annular base (220) to the initial lock position (see FIG. 6), thereby frictionally engaging cannula tube (22, 124) and locking depth limiter (200) relative to cannula tube (22, 124) at the selected longitudinal position. Should the clinician wish to more securely lock depth limiter (200) at the selected longitudinal position, the clinician may then depress tang (252) downwardly to force latch arm (218) into the full lock position shown in FIG. 8A and described above.

Latch arm (218) may have a varying degree of lock positions between the initial lock position (see FIGS. 6-7) and the full lock position (see FIG. 8A). In order to transition depth limiter (200) distally from a first lock position (e.g., the initial lock position) to second lock position (e.g., the full lock position), a clinician applies a distal force to tang (252), which in turn increases the degree of frictional engagement and thus locking force between latch arm (218) and cannula tube (22, 124).

It will be appreciated that the degree of frictional engagement between latch arm (218) and cannula tube (22, 124) in the initial lock position is high enough to resist low relative axial loads exerted between depth limiter (200) and cannula tube (22, 124), for example during distal insertion of the corresponding cannula assembly (12, 112) through an abdominal wall (2) of patient. In some versions, this degree of frictional engagement in the initial lock position may also low enough to permit a clinician to intentionally pull depth limiter (200) off of cannula tube (22, 124) without first lifting latch arm (218) to the release position. For instance, the clinician may remove depth limiter (200) from cannula tube (22, 124) by grasping cannula assembly (12, 112) with one hand and annular base (220) of depth limiter (200) with the other hand, and pulling cannula assembly (12, 112) proximally while simultaneously pulling annular base (220) distally. This process will automatically force latch arm (218) to release the position, thus enabling depth limiter (200) to translate distally along cannula tube (22, 124).

B. Second Exemplary Depth Limiter Having Spring Latch Arm

Figure 9:
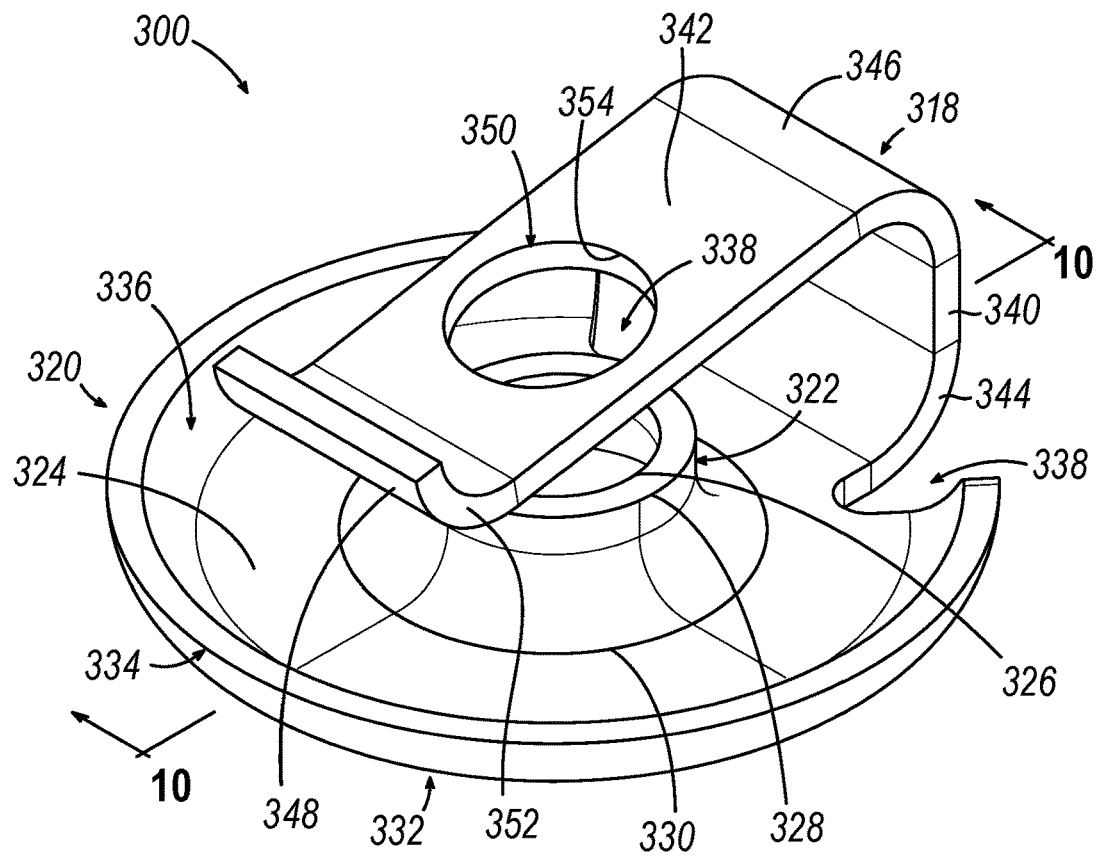
FIG. 9 depicts a perspective view of a second exemplary depth limiter, showing a latch arm of the depth limiter in an initial lock position that inhibits relative translation between the depth limiter and a cannula tube.
Figure 10:
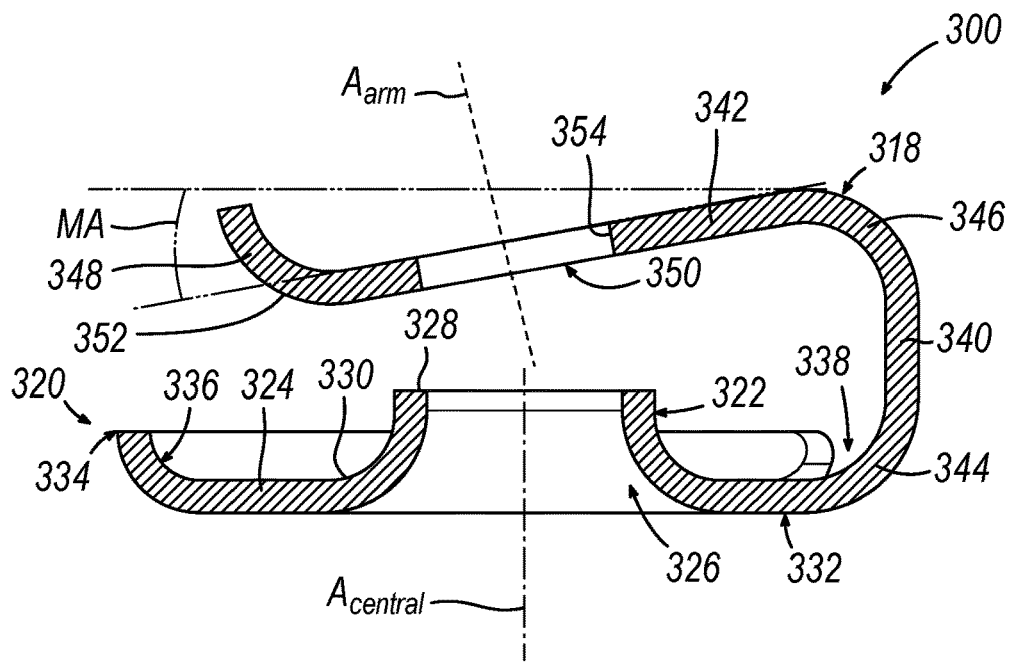
FIG. 10 depicts a side sectional view of the depth limiter of FIG. 9, showing the latch arm in the initial lock position.

In some instances, it may be desirable to provide a version of cannula depth limiter (200) in which latch arm (218) is not limited to a maximum deflection angle (MA) by proximal face (228) of central boss (222). FIG. 9-10 shows another exemplary depth limiter (300) that exhibits such a configuration. As described in greater detail below, depth limiter (300) may selectively limit depth to which trocar (10, 110) may travel distally into abdominal wall (2). Depth limiter (300) is substantially similar to depth limiter (200) described above except where explicitly noted herein.

Like with depth limiter (200), depth limiter (300) includes a latch arm (318) pivotally coupled to an annular base (320). Latch arm (318) is flexible relative to annular base (320) and may be moved from a release position, to at least one initial lock position, and further to a full lock position. Annular base (320) is relatively rigid and includes a central boss (322) and an annular hub (324). Central boss (322) defines a boss lumen (326) that extends distally along a central axis ($A_{central}$) from a proximal face (328) to a distal portion (330). Annular hub (324) includes an underside (332) that extends radially to an outer edge (334). Outer edge (334) has a pair of relief cut features (338) proximal to latch arm (318).

Latch arm (318) is operatively attached to outer edge (334) between a pair of relief cut features (338) at a first bend (344). First bend (344) attaches first arm portion (340) to annular base (320). First arm portion (340) extends proximally to second bend (346). Second bend (346) curves transverse to central axis ($A_{central}$) and attaches to second arm portion (342). Second arm portion (342) extends towards central axis ($A_{central}$) and overlies the central boss (322). Second arm portion (342) defines an arm opening (350) and includes a tang (352). Arm opening (350) has an arm axis ($A_{arm}$) centrally located within arm opening (350) and perpendicular to annular base (320). Arm opening (350) has an inner edge (354) that may have an engagement feature (not shown). Like latch arm (218), latch arm (318) is resiliently biased toward the initial lock position shown in FIGS. 9 and 10.

Depth limiter (300) differs from depth limiter (200) in that central boss (322) is formed with a shorter axial height than central boss (222), and with a proximal face (328) that is generally parallel to annular base (332). Consequently, proximal face (328) of central boss (322) does not limit latch arm (318) to a maximum deflection angle (MA) when depth limiter (300) is coupled with a cannula tube (22, 124). Specifically, latch arm (318) is not configured to engage proximal face (328) in the full lock position. Latch arm (318) may still travel until arm axis ($A_{arm}$) is at a maximum deflection angle (MA), but maximum deflection angle (MA)

will not be defined by proximal face (328). Rather, the maximum deflection angle (MA) of latch arm (318) during use may be defined by the point at which latch arm (318) achieves a maximum possible degree of frictional engagement with the outer surface of cannula tube (22, 124). This configuration of depth limiter (300) may functional substantially similar to depth limiter (200), while being easier to manufacture due to the simplified shape of central boss (322).

C. Third Exemplary Depth Limiter Having Pivotable Latch Arm

Figure 11:
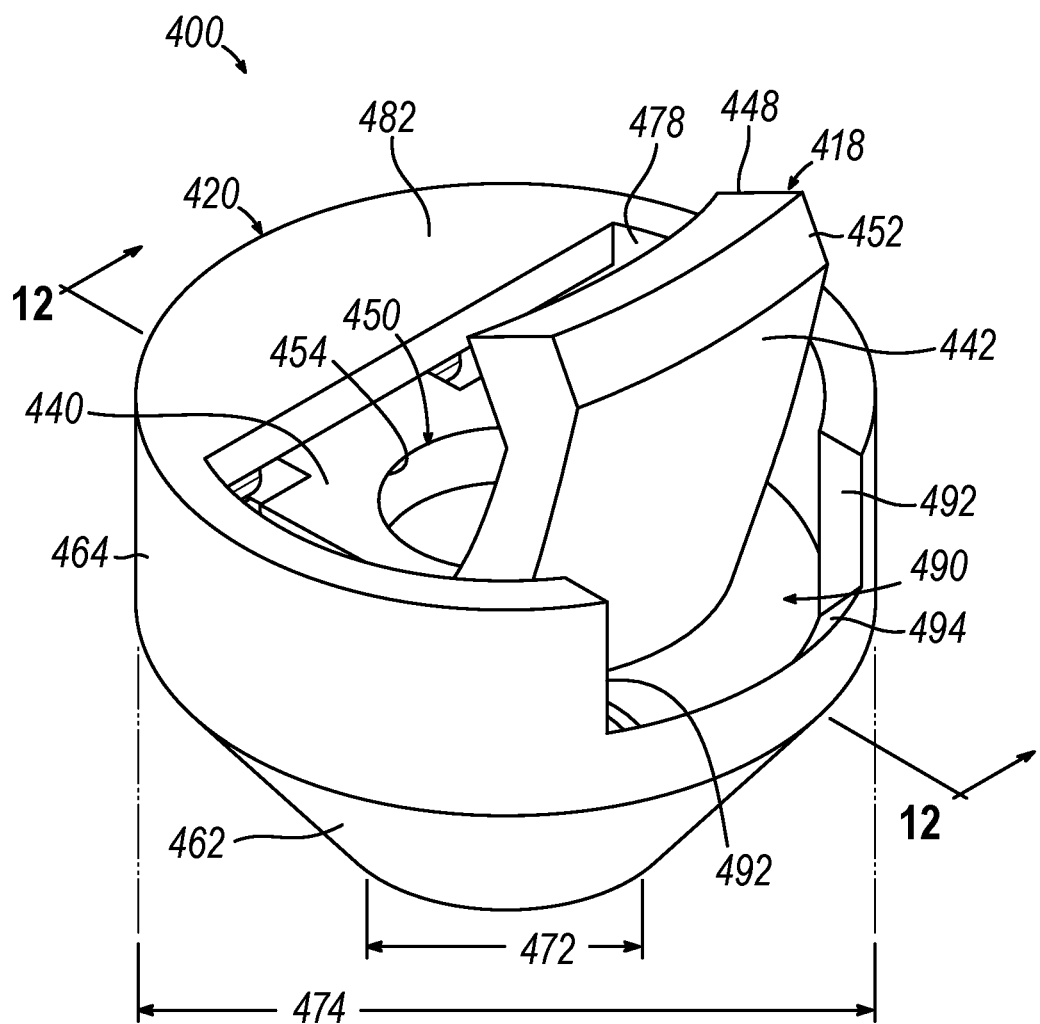
FIG. 11 depicts a perspective view of a third exemplary depth limiter, showing a latch arm of the depth limiter in a release position that permits relative translation between the depth limiter and a cannula tube of a trocar.
Figure 12A:
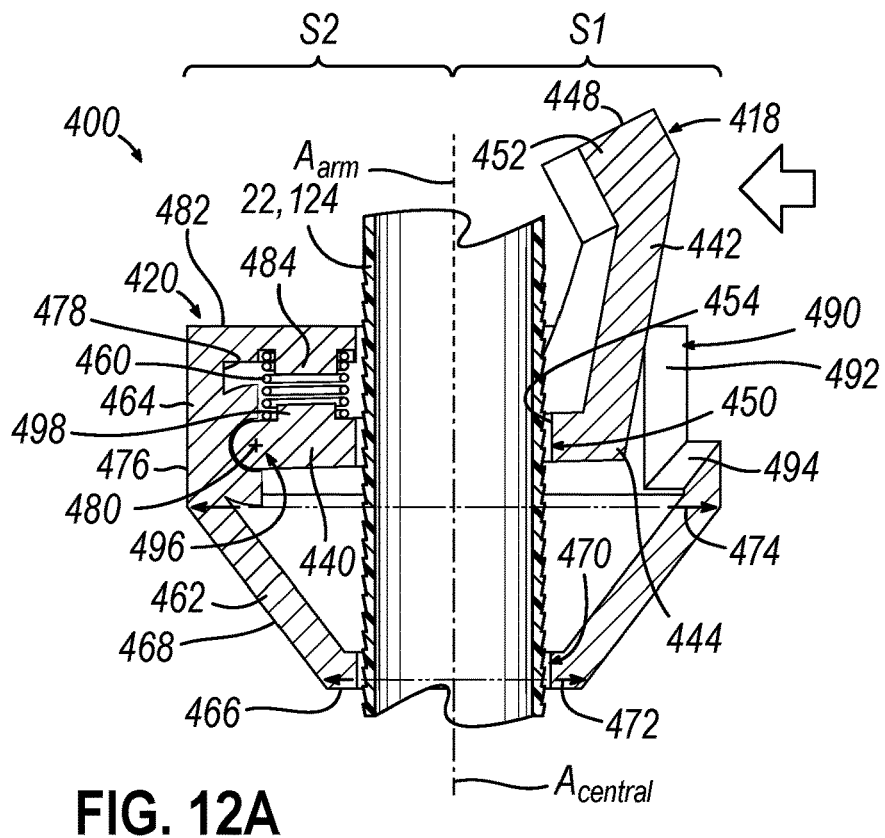
FIG. 12A depicts a side sectional view of the depth limiter of FIG. 11 coupled with the cannula tube of FIG. 4, showing the latch arm in the release position to permit relative translation between the depth limiter and the cannula tube.
Figure 12B:
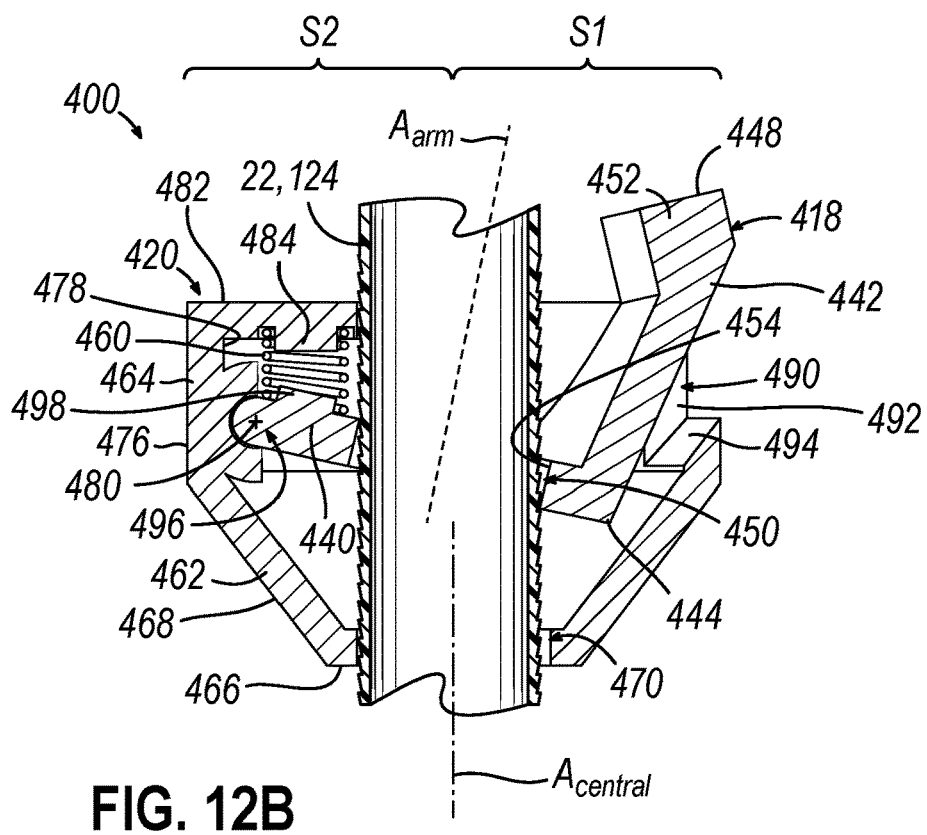
FIG. 12B depicts a side sectional view of the depth limiter of FIG. 11 and the cannula tube of FIG. 4, showing the latch arm in a lock position that inhibits relative translation between the depth limiter and the cannula tube.

In some instances, it may be desirable to provide a cannula depth limiter with a housing that tapers distally and includes a latch arm that is rigid and is resiliently biased toward a locked position. FIGS. 11-12B shows an exemplary depth limiter (400) configured in this manner. As described in greater detail below, depth limiter (400) may selectively limit a depth to which trocar (10, 110) may travel into abdominal wall (2). Like depth limiters (200, 300), depth limiter (400) includes a latch arm (418) pivotally coupled to a housing (420), and latch arm (418) is resiliently biased to a lock position. Latch arm (418) includes an arm opening (450) having an inner edge (454) similar to inner edge (254) of depth limiter (200). In some versions, inner edge (454) may include an engagement feature (not shown) that has complementary geometric features to ribs (26, 128) of cannula tube (22, 124). Latch arm (418) may be manipulated with a thumb or finger to transition between a release position (see FIG. 12A) in which latch arm (418) permits relative longitudinal movement between depth limiter (400) and cannula tube (22, 124); and at least one lock position (see FIG. 12B) in which latch arm (418) inhibits relative longitudinal movement between depth limiter (400) and cannula tube (22, 124).

Depth limiter (400) differs from depth limiter (200) in that depth limiter (400) includes a housing (420) that at least partially houses latch arm (418), and the bias of latch arm (418) is provided by an independent biasing member shown in the form of a compression spring (460). Housing (420) may have any suitable shape that is capable of supporting latch arm (418) relative to a cannula tube (22, 124). In the example shown, housing (420) includes a distal frustoconical portion (462) and a proximal cylindrical portion (464). A proximal end of proximal cylindrical portion (464) may be suitably contoured to mate with the distal end of a trocar cannula hub, such as hub (122) of reusable cannula assembly (112), or otherwise the distal end of a trocar seal assembly, such as seal assembly (30) of disposable cannula assembly (12).

Frustoconical portion (462) includes a truncated distal face (466) and a conical portion (468). Truncated face (466) defines a distal bore (470) that opens to an interior of the body defined by housing (420) and which lies along central axis ($A_{central}$) and is sized to slidably receive cannula tube (22, 124) of trocar (10, 110). Conical portion (468) extends proximally along central axis ($A_{central}$) from truncated face (466). Conical portion (468) tapers from a distally located first diameter (472) to a proximally located second diameter (474). First diameter (472) is smaller relative to second diameter (474). Cylindrical portion (464) includes an outer wall (476), an inner wall (478), a pivot point (480), and a proximal face (482). Outer wall (476) extends proximally from second diameter (474) of conical portion (468) along the central axis ($A_{central}$) to proximal face (482). Outer wall (476) has the second diameter (474) for its entire length. Proximal face (482) partially covers the top of cylindrical portion (464) and includes a spring retainer (484) located on an inside of the proximal face (482). Spring retainer (484) may include a central pin (486), an annular recess (488), or a locking tab (not shown) to secure spring (460) to the inside of the proximal face (482). Spring retainer (484) prevents spring (460) from inadvertently being discharged from proximal face (482) of housing (420).

Cylindrical portion (464) defines a relief slot (490) located on a first side (S1) of central axis ($A_{central}$). Relief slot (490) includes a pair of vertical faces (492) and a horizontal face (494) that extend radially from inner wall (478) to outer wall (476). Horizontal face (494) connects pair of vertical faces (492) distal of proximal face (482). Horizontal face (494) may be tapered to engage latch arm (418) in full lock position at a maximum deflection angle (MA). Relief slot (490) is sized to allow latch arm (418) to pivot about pivot point (480) radially outwardly through a circle defined by inner wall (478) and further pass through a circle defined by outer wall (476). Relief slot (490) is sized to accept latch arm (418) in a full range of motion from release position (see FIG. 12A), to a lock position (see FIG. 12B).

Pivot point (480) pivotably couples to latch arm (418) on a second side (S2) of central axis ($A_{central}$) that is opposite first side (S1) and relief slot (490). Pivot point (480) is operatively attached inner wall (478). In the present version, pivot point (480) is integral with inner wall (478). Pivot point (480) may include a snap fitting (not shown), a pin (not shown), a transverse bore (not shown), a living hinge (not shown) or any other structure capable of pivotably coupling a planar moving part to a rigid housing apparent to those of ordinary skill in the art.

Latch arm (418) includes a first arm portion (440), and a second arm portion (442). First arm portion (440) includes a pivot feature (496), a spring engagement feature (498), an arm opening (450), and a first bend (444). Pivot feature (496) pivotally couples to pivot point (480). First arm portion (440) extends from pivot feature (496) to free end (448). First arm portion (440) defines a circular arm opening (450) that overlies distal bore (470). Arm opening (450) includes an arm axis ($A_{arm}$) centrally located within arm opening (450).

Spring engagement feature (498) (see FIG. 12A-12B), is located on second side (S2) of central axis ($A_{central}$) on an upper portion of first arm portion (440) that corresponds with the location of spring (460). In the present version, depth limiter (400) is biased to an initial lock position (see FIG. 12A). Spring engagement feature (498) may include a central pin, an annular recess (not shown), a locking tab (not shown) or any other structure that may secure a spring (460) apparent to those in the art.

In other versions, spring engagement feature (498) may be located on a lower portion of first arm portion (440) and correspond with a similarly situated spring retainer (484) to bias depth limiter (400) to release position. In yet other versions, spring engagement feature (498) may be located on first side (S1) of central axis ($A_{central}$).

Second arm portion (442) extends from first bend (444) in proximal direction to a free end (448). Second arm portion (442) may have a cross-section that is arcuate or flat. Horizontal face (494) will also be arcuate if second arm portion (442) has an arcuate cross-section. Free end (448) includes tang (452) having a slight bend relative to second arm portion (442).

FIG. 12A shows latch arm (418) of depth limiter (400) being held in a proximal, release position. From the lock position shown in FIG. 12B, a clinician uses a thumb or finger to rotate tang (452) in an arcuate proximal direction about pivot point (480) toward cannula tube (22, 124), thereby overcoming the opposing bias of compression spring (460). Latch arm (418) compresses spring (460) between spring retainer (484) and spring engagement feature (498). As first arm portion (440) pivots to an angle that is generally perpendicular to central axis ($A_{central}$), arm opening (450) aligns concentrically with distal bore (470) such that arm axis ($A_{arm}$) is coaxial with central axis ($A_{central}$). Inner edge (454) of the arm opening (450) no longer engages cannula tube (22, 124), thereby enabling depth limiter (400) to be moved axially along cannula tube (22, 124).

FIG. 12B shows latch arm (418) of depth limiter (400) in a lock position. Latch arm (418) is transitioned to the lock position from the release position of FIG. 12A simply by releasing the user's thumb or finger from tang (452). Once released, spring (460) biases spring engagement feature (498) distally, thereby rotating first arm portion (440) about pivot point (480). Inner edge (454) of arm opening (450) re-engages cannula tube (22, 124) as arm axis ($A_{arm}$) no longer aligns with central axis ($A_{central}$), thereby locking depth limiter (400) axially relative to cannula tube (22, 124). In some versions, depth limiter (400) may further include one or more detent features (not shown) configured to releasably maintain latch arm (418) in the release position and/or the lock position until latch arm (418) is actuated away from the detented position by the clinician.

In some versions, latch arm (418) may be movable relative to housing (420) between multiple lock positions, such as an initial lock position and a full lock position. For instance, the position of latch arm (418) shown in FIGS. 11 and 12B may constitute an initial lock position, such that latch arm (418) may be further transitioned to a full lock position by pressing tang (452) further distally, and radially outwardly, with a thumb or finger. Latch arm (418) will rotate about pivot point (480) in an arcuate manner until second arm portion (442) engages horizontal face (494) at the maximum deflection angle (MA). Horizontal face (494) will prevent inner edge (454) from over engaging cannula tube (22, 124). Arm axis ($A_{arm}$) will be further angled relative to central axis ($A_{central}$), making arm opening (450) less aligned with distal bore (470). The increased differential of alignment between central axis ($A_{central}$) and arm axis ($A_{arm}$) results in greater frictional engagement and resulting locking force between inner edge (454) of latch arm (418) and the outer surface of cannula tube (22, 124).

D. Fourth Exemplary Depth Limiter

Figure 13:
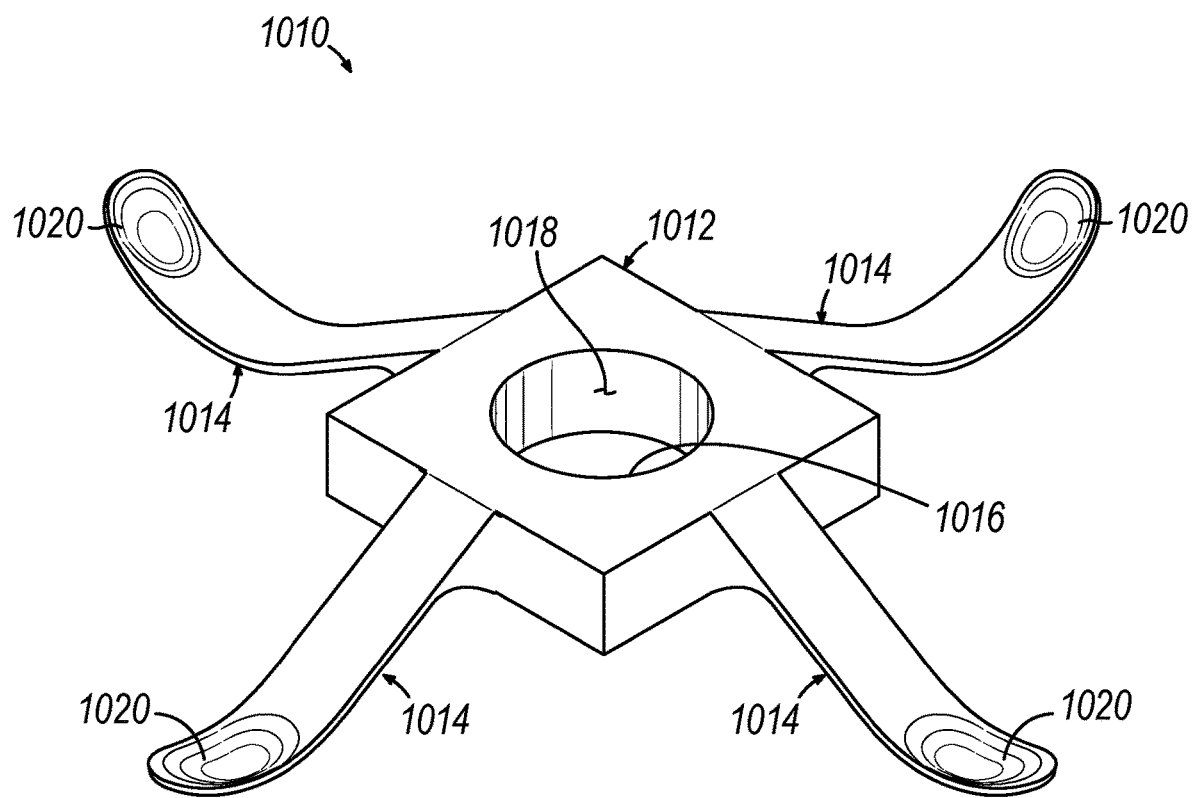
FIG. 13 depicts a perspective view of a fourth exemplary depth limiter that includes four legs.

FIG. 13 shows a perspective view of a fourth exemplary depth limiter (1010). Depth limiter (1010) includes a hub (1012) and a plurality of legs (1014). Depth limiter (1010) may be used in combination with depth limiters (200, 300, 400) described above. While hub (1012) is shown as being generally square shaped, other shapes of hub (1012) are also envisioned. As shown, hub (1012) includes an aperture (1016) extending completely therethrough. Aperture (1016) may include a gripping surface (1018). Gripping surface (1018) may extend parallel to a longitudinal axis defined by cannula tube (22) of cannula (20). While FIGS. 13-14B describe depth limiter (1010) with reference to cannula tube (22) of trocar (10) of FIG. 1, other cannula tubes (e.g., cannula tube (124)) may also be used. Gripping surface (1018) may be smooth or non-smooth. As shown in FIG. 13, gripping surface (1018) includes a smooth surface that may frictionally engage a portion of cannula (20), such as ribs (26). Alternatively, gripping surface (1018) may include a non-smooth surface may include one or more features to lockingly engage cannula tube (22). In other words, depth limiter (1010) may be secured to cannula (20) with mating threads (like a nut) or secured to a scalloped cannula with an appropriate amount of interference fit. Such threads of depth limiter (1010) may be helical or non-helical (e.g., scallops). For example, gripping surface (1018) may include at least one tooth configured to lockingly engage with at least one of rib (26) of cannula (20).

Legs (1014) may have a generally constant cross-sectional area moving radially away from hub (1012); however, legs (1014) may have a non-uniform cross-section. For example, one or more ends of legs (1014) may include cupped portions (1020) to distribute the downward force. As shown, legs (1014) are separated by approximately 90 degrees. More or fewer legs (1014) are also envisioned.

Depth limiter (1010) may provide additional stability to the trocar (10) for anti-tip resistance. Depth limiter (1010) may be configured to restrict sudden tilting using legs (1014), thereby stabilizing cannula (20). Depth limiter (1010) is configured to prevent accidental over-insertion into body, while also restricting the displacement and/or velocity of off-axis tilting of trocar (10) to stabilize trocar (10). This stabilization may be achieved using mechanical spring effects of each leg (1014). Legs (1014) may have a reduced mass allowing legs (1014) to flex outwardly, causing a variable amount of spring-resistance in each direction that trocar (10) attempts to tilt. For example, legs (1014) may have reduced mass portions (e.g., living hinge portions), and/or may rely on inherent spring force of legs (1014). Legs (1014) may contact the patient's body wall to prevent or at least decelerate tip over of cannula (120).

Figure 14A:
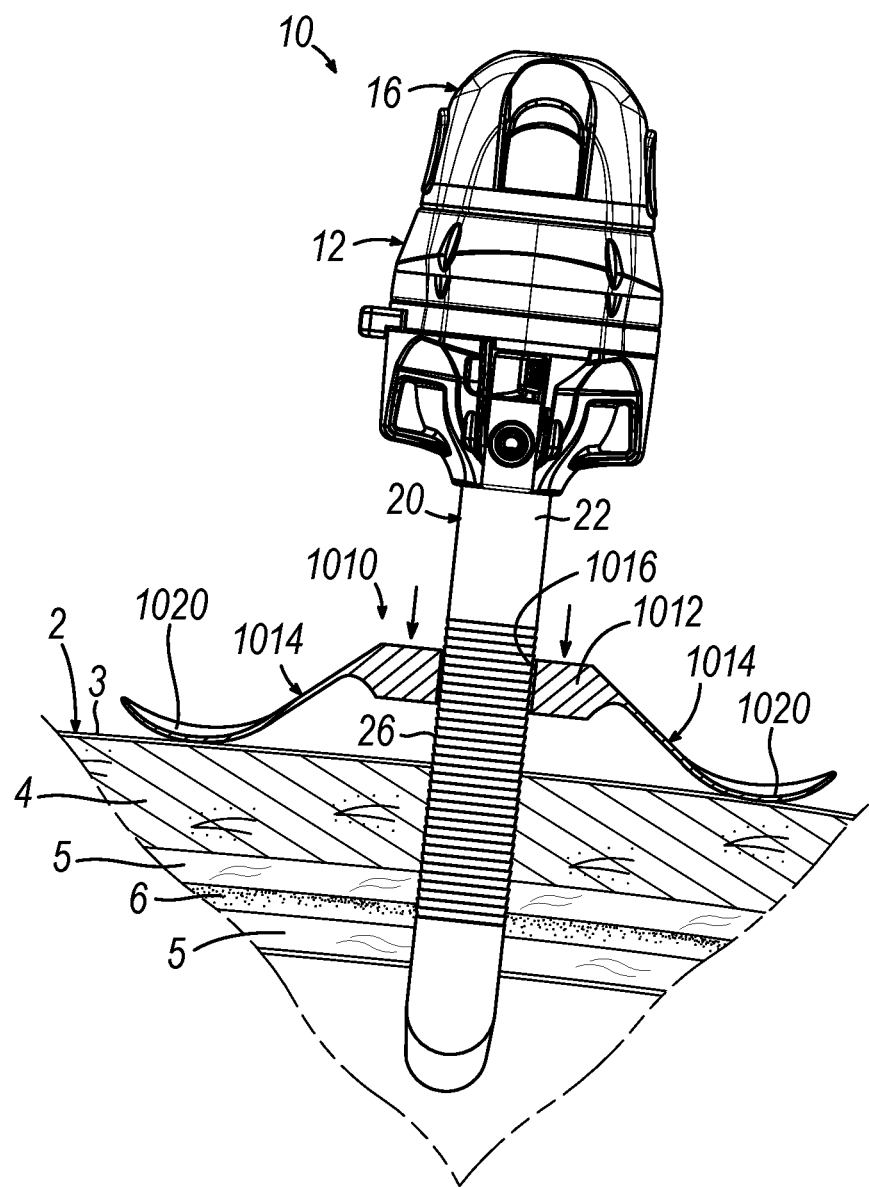
FIG. 14A depicts a partial side sectional view of the depth limiter of FIG. 13 coupled with the cannula tube of the cannula assembly of the trocar of FIG. 1, where the legs of the depth limiter are in a non-deployed configuration when the distal end of the trocar received within the abdominal cavity.
Figure 14B:
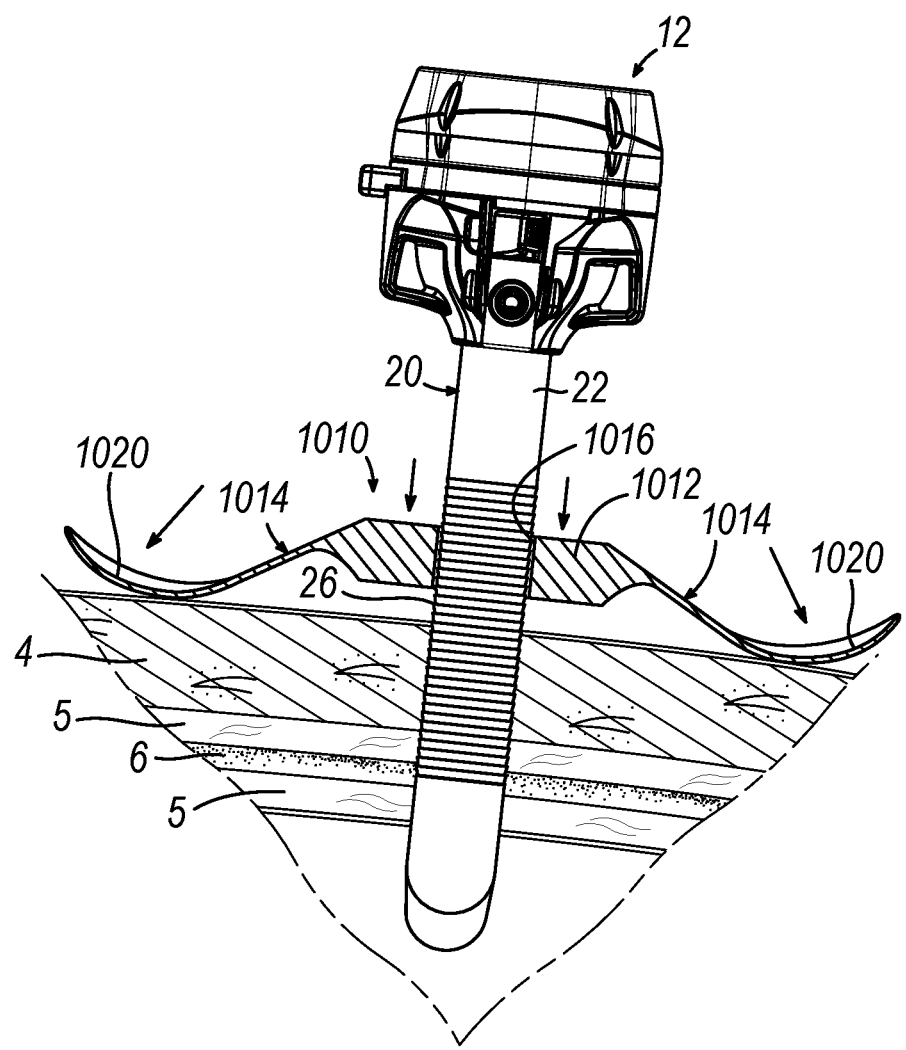
FIG. 14B depicts a partial side sectional view of the depth limiter of FIG. 13 coupled with the cannula tube of the cannula assembly of FIG. 1 following detachment and removal of the obturator, where the legs of the depth limiter are in a deployed configuration with a distal end of the cannula tube received within the abdominal cavity.

FIGS. 14A-14B show depth limiter (1010); however, the teachings of FIGS. 14A-14B may also apply to depth limiters (1110, 1210) described in detail below. FIG. 14A shows a partial side sectional view of depth limiter (1010) of FIG. 13 coupled with cannula tube (22) of cannula assembly (12) of trocar (10) of FIG. 1, where legs (1014) of depth limiter (1010) are in a non-deployed configuration when distal end of trocar (10) received within abdominal cavity (1). In the non-deployed configuration (e.g., the resting configuration) of FIG. 14A, legs (1014) may be curved downwardly. As depth limiter (1010) is pushed against abdominal wall (2), legs (1014) bend flatter and provide reaction spring-forces against abdominal wall (2) and cannula (20). The degree at which legs (1014) bend flatter may be controlled by the user. For example, additional force (e.g., downward hand pressure by the user) may cause legs (1014) to bend flatter until depth limiter (1010) is disposed adjacent to abdominal wall (2). As the flatness of legs (1014) increases, the amount of reactive forces on cannula (20) may also increase, which increases the locking force. For example, when the user has depressed depth limiter (1010) to a partially (but not fully) deployed configuration, legs (1014) may have some degree of deployment. Additionally, if the user then applies an off-axis loading, one or more of legs (1014) may depress further than the other legs (1014), but upon removal of the off-axis load, legs (1014) may be equalized and return in a controlled manner to a centered home position.

FIG. 14B shows a partial side sectional view of depth limiter (1010) of FIG. 13 coupled with cannula tube (22) of cannula assembly (12) of FIG. 1 following detachment and removal of obturator (16), where legs (1014) of depth limiter (1010) are in a deployed configuration with a distal end of cannula tube (22) received within abdominal cavity (1). In the deployed configuration, legs (1014) may reduce the amount of rotational displacement/tilt that trocar (10)) may achieve, and may also reduce the velocity that trocar (10) may achieve that tilt (i.e., preventing sudden accidental moves within the body). To completely undeploy depth limiter (1010) from cannula tube (22), the user may retract cannula (20) out of abdominal wall (2) to sufficiently reduce the compressive/clamping forces of depth limiter (1010) on the abdominal wall (2), such that the user may pull the depth limiter (1010) back using their hand. Depth limiter (1010) may be disposable or re-usable.

E. Fifth Exemplary Depth Limiter

Figure 15:
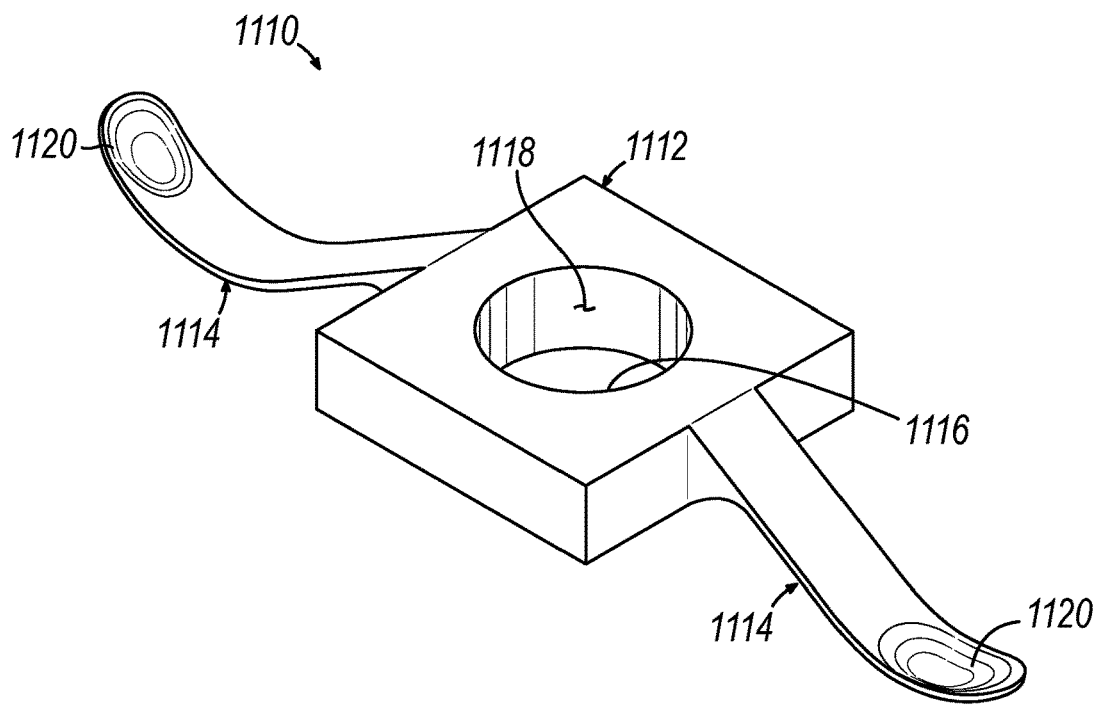
FIG. 15 depicts a perspective view of a fifth exemplary depth limiter that includes two legs.

FIG. 15 shows a fifth exemplary depth limiter (1110) that is similar to depth limiter (1010). Depth limiter (1110) includes a hub (1112) similar to hub (1012), legs (1114) similar to legs (1014), an aperture (1116) similar to aperture (1016), a gripping surface (1118) of aperture (1116) similar to gripping surface (1018). Legs (1114) may include cupped portions (1120) similar to cupped portions (1020). Unlike depth limiter (1010) that is shown as including four legs (1014), depth limiter (1110) includes two legs (1114). For example, legs (1114) may be separated by approximately 180 degrees. Legs (1114) flex similar to legs (1014) shown above with reference to FIGS. 14A-14B.

F. Sixth Exemplary Depth Limiter

Figure 16:
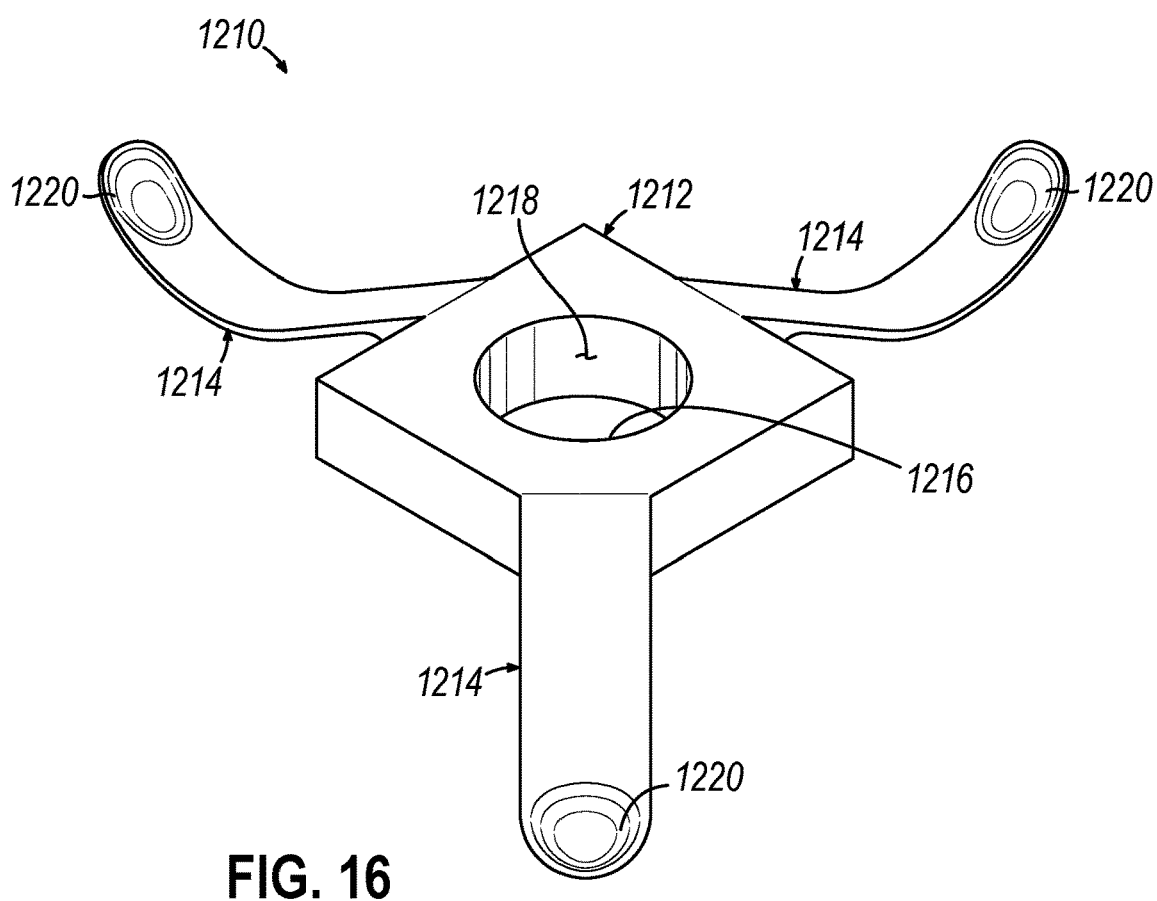
FIG. 16 depicts a perspective view of a sixth exemplary depth limiter that includes three legs.

FIG. 16 shows an sixth exemplary depth limiter (1210) that is similar to depth limiters (1010, 1110). Depth limiter (1210) includes a hub (1212) similar to hub (1012), legs (1214) similar to legs (1014), an aperture (1216) similar to aperture (1016), a gripping surface (1218) of aperture (1216) similar to gripping surface (1018). Legs (1114) may include cupped portions (1220) similar to cupped portions (1020). Unlike depth limiter (1010) that is shown as including four legs (1014), depth limiter (1210) includes three legs (1214). For example, legs (1214) may be circumferentially separated uniformly by approximately 120 degrees around hub (1212). However, legs (1214) may be non-uniformly separated. In some instances, the use of three or four legs (1014, 1214, 1314, 1414) may allow for further stability and ergonomics to allow for finger grip of user (U). Legs (1214) may flex similar to legs (1014) shown above with reference to FIGS. 14A-14B.

G. Seventh Exemplary Depth Limiter

FIGS. 17-19B show a seventh exemplary depth limiter (1310). Particularly, FIG. 17 shows a perspective view of depth limiter (1310). As shown, depth limiter (1310) includes a hub (1312) and a plurality of legs (1314). extending from hub (1312). Depth limiter (1310) may be used in combination with any one or more of depth limiters (200, 300, 400) described above. While hub (1312) is shown as being generally cylindrically shaped, other shapes of hub (1312) are also envisioned. As shown, hub (1312) includes an aperture (1316) and a plurality of notches (1318). Notches (1318) may transform depth limiter (1310) from a movable configuration to a fixed configuration.

Aperture (1316) includes a gripping surface (1320) that is configured to couple with the outer surface of cannula tube (124) in the fixed configuration. Gripping surface (1320) may extend parallel to a longitudinal axis defined by cannula tube (124) of cannula (120). While FIGS. 18A-19B describe depth limiter (1310) with reference to cannula tube (124) of trocar (110), other cannula tubes (e.g., cannula tube (22)) may also be used. Gripping surface (1320) may be smooth or non-smooth. As shown in FIG. 17, gripping surface (1320) may include a smooth surface that frictionally engages ribs (128) of cannula (120) in the fixed configuration. Alternatively, gripping surface (1320) may include a non-smooth surface may include one or more features to lockingly engage cannula tube (124). Hub (1312) of depth limiter (1310) may be secured to cannula (120) with mating threads (like a nut) or may be secured to a scalloped cannula using an interference fit. Threads may be helical or non-helical (e.g., scallops). For example, gripping surface (1320) may include at least one tooth configured to lockingly engage with at least one of rib (128) of cannula (120). For example, notches (1318) may be formed in hub (1312) of depth limiter (1310), such that each leg (1314) may selectively collapse when adequate force acts on that leg (1314), causing gripping surface (1320) to clamp down tighter on cannula (120). As such, depth limiter (1310) may limit insertion depth of cannula tube (124) of cannula (120) and provide stability control of cannula tube (124) of cannula (120).

Legs (1314) may have a generally tapering cross-section moving radially away from hub (1312). For example, one or more ends of legs (1314) may include distal pad (1122) to distribute the downward force. As shown, legs (1314) are separated by approximately 90 degrees. Legs (1314) may be non-uniformly separated. Additionally, more or fewer legs (1314) are also envisioned (similar to those shown in FIGS. 16-17 associated with depth limiters (1310, 1410). Depth limiter (1310) may provide additional stability to the trocar (110) for anti-tip resistance. Depth limiter (1310) may be configured to restrict sudden tilting using legs (1314), thereby stabilizing cannula (120). Legs (1314) may contact body wall to prevent or at least decelerate tip over of cannula (120).

Figure 19A:
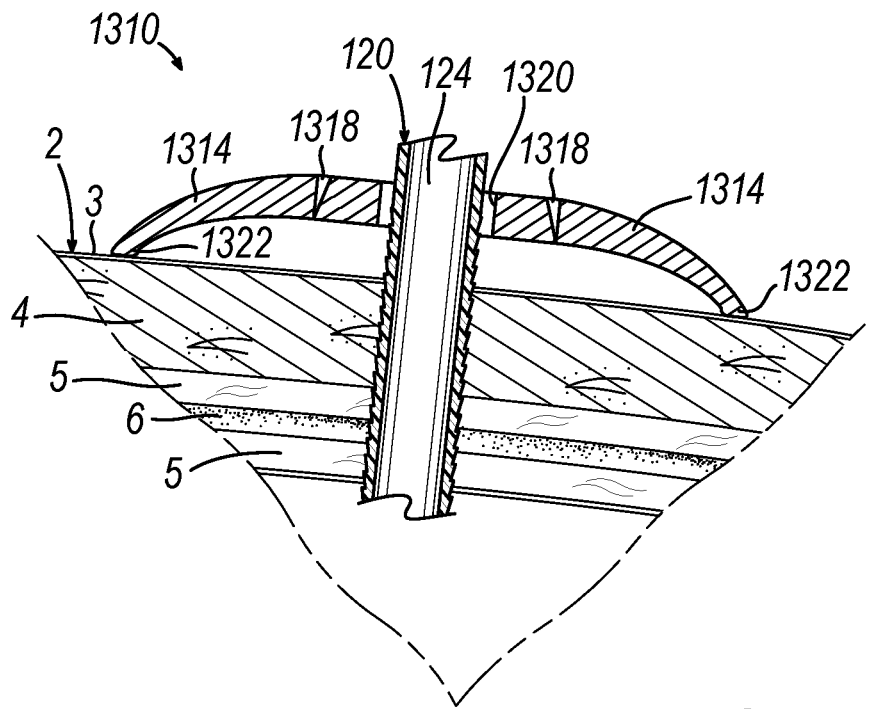
FIG. 19A depicts a partial side sectional view of the depth limiter of FIG. 17 coupled with the cannula tube of the cannula assembly of FIG. 5, where the legs of the depth limiter are in a non-deployed configuration.

FIGS. 18A and 19A show depth limiter (1310) in the movable configuration. Particularly, FIG. 18A shows a top plan view of depth limiter (1310) of FIG. 17 coupled with cannula tube (124) of cannula assembly (112) of FIG. 5, where hub (1312) of depth limiter (1310) is in a movable configuration. FIG. 19A shows a partial side sectional view of depth limiter (1310) of FIG. 17 coupled with cannula tube (124) of cannula assembly (112) of FIG. 5, where legs (1314) of depth limiter (1310) are in the movable configuration. In the movable configuration of FIGS. 18A and 19A, gripping surfaces (1320) collectively form a second effective diameter (ED2) that allows for axial movement of depth limiter (1310) relative to an outer diameter of cannula tube (124) of cannula assembly (112). In the movable configuration, also considered the resting configuration, legs (1314) are curved downwardly. Once pushed against abdominal wall (2), legs (1314) bend flatter and provide a reaction force against abdominal wall (2) and cannula (120).

Figure 19B:
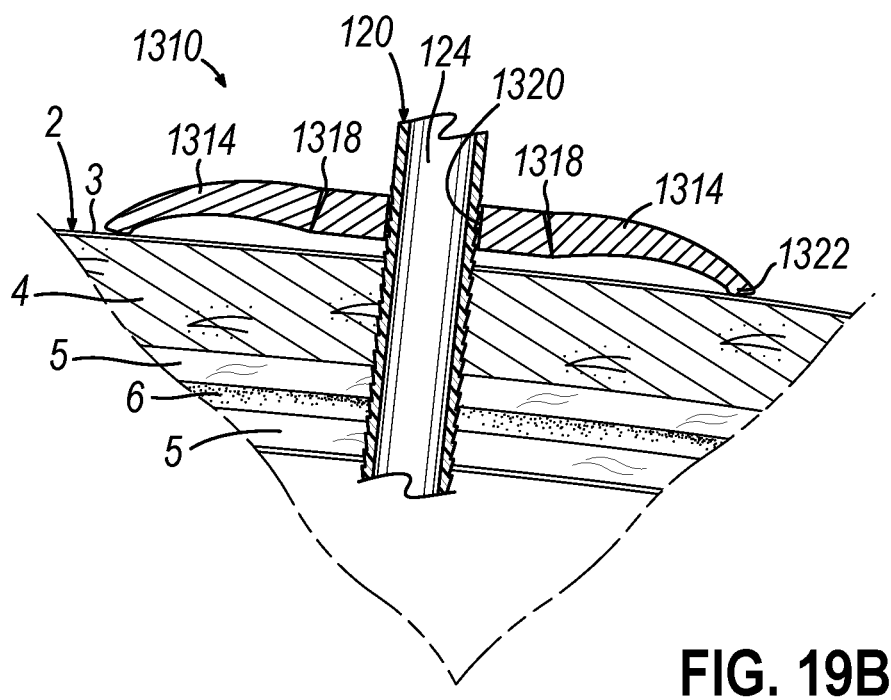
FIG. 19B depicts a partial side sectional view of the depth limiter of FIG. 17 coupled with the cannula tube of the cannula assembly of FIG. 5 following detachment and removal of the obturator, where the legs of the depth limiter are in a non-deployed configuration.

FIGS. 18B and 19B show depth limiter (1310) in the movable configuration. Particularly, FIG. 18B shows a partial side sectional view of depth limiter (1310) of FIG. 17 coupled with cannula tube (124) of cannula assembly (112) of FIG. 5 following detachment and removal of obturator (116), where legs (1314) of depth limiter (1310) are in the fixed configuration. FIG. 19B shows a partial side sectional view of depth limiter (1310) of FIG. 17 coupled with cannula tube (124) of cannula assembly (112) of FIG. 5 following detachment and removal of obturator (116), where legs (1314) of depth limiter (1310) are in the fixed configuration. In the fixed configuration, notches (1318) may be forced closed to narrow aperture (1316). Legs (1314) may reduce the amount of rotational displacement/tilt that trocar (110)) may exhibit, and may also reduce the velocity at which trocar (110) may assume that tilt (i.e., preventing sudden movements within the body). In the fixed configuration, gripping surfaces (1320) collectively form a first effective diameter (ED1) that restricts axial movement of depth limiter (1310) relative to cannula (120) by directly contacting cannula (120). Depth limiter (1310) may be disposable or reusable.

H. Eighth Exemplary Depth Limiter

Figure 20:
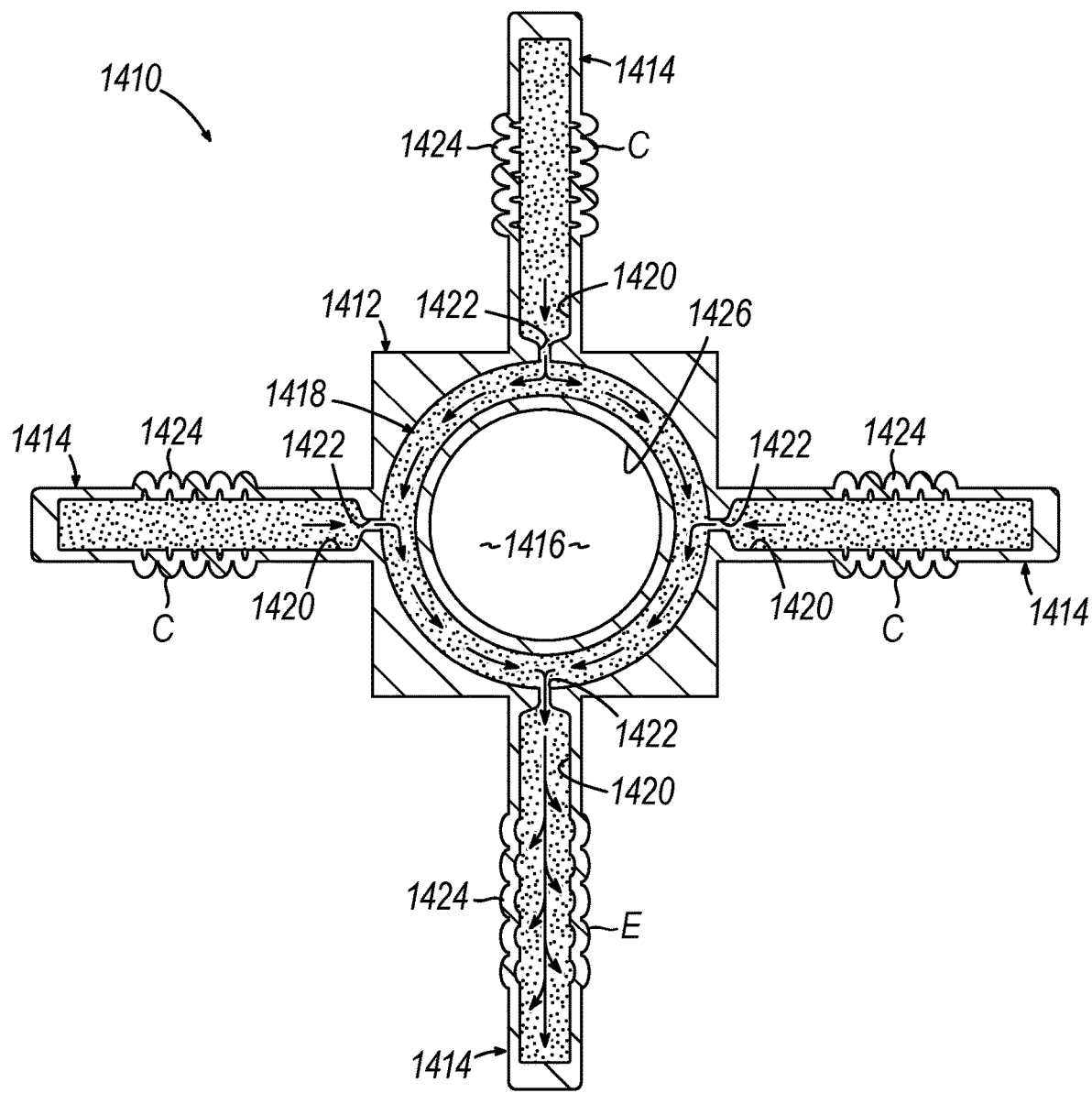
FIG. 20 depicts a top sectional view of an eighth exemplary depth limiter that includes a fluid chamber and four legs.

FIG. 20 shows a top sectional view of an eighth exemplary depth limiter (1410). Depth limiter (1410) includes a hub (1412) and a plurality of legs (1414) extending from hub (1412). Depth limiter (1410) may be used in combination with any one or more of depth limiters (200, 300, 400) described above. In some versions, hub (1412) may being generally cylindrically shaped. As shown, hub (1412) includes an aperture (1416) configured to receive cannula tube (124) of cannula (120). As shown, legs (1414) may be separated by approximately 90 degrees. However, legs (1414) may be non-uniformly separated. Additionally, more or fewer legs (1414) are also envisioned, similar to those shown in FIGS. 14-15 associated with depth limiters (1110, 1210).

Depth limiter (1410) includes a fluid chamber (1418) that may be disposed within hub (1412) and legs (1414). For example, fluid chamber (1418) may be completely enclosed by hub (1412) and legs (1414). Fluid chamber may include a plurality of fluid passageways (1420) that include narrow portions (1422). Narrow portions (1422) may be disposed generally between hub (1412) and legs (1414). Narrow portions (1422) regulate flow between hub (1412) and legs (1414). In other words, fluid chamber (1418) may be integrated into legs (1414) with narrow portions (1422) forming restricted areas of flow at the base of each leg (1414). As shown, one or more ends of legs (1414) may include extensive portion (1424) configured to extend from a compressed configuration (C) to an expanded configuration (E). Depth limiter (1410) may provide additional stability to the trocar (110) for anti-tip resistance. As additional tilt force acts on each independent leg (1414), the fluid may redistribute to the other legs (1414), but the fluid may be restricted by these narrow portions (1422), thus creating a damping effect on the tilting of trocar (110). This damping effect may regulate the speed at which trocar (110) tilts. As a result, depth limiter (1410) may restrict sudden tilting of trocar (110) via restricted fluid flow between legs (1414), thereby stabilizing cannula (120).

Aperture (1416) includes a gripping surface (1426) that may couple with the outer surface of cannula tube (124) of cannula (120). Gripping surface (1426) may extend parallel to a longitudinal axis defined by cannula tube (124) of cannula (120). Gripping surface (1426) may be smooth or non-smooth. As shown in FIG. 20, gripping surface (1426) may include a smooth surface that frictionally engages ribs (128) of cannula (120). Alternatively, gripping surface (1426) may include a non-smooth surface may include one or more features to lockingly engage cannula tube (124). For example, hub (1412) of depth limiter (1410) may be secured to cannula (120) using mating threads (like a nut) or secured to a scalloped cannula. Threads may be helical or non-helical (e.g., scallops). For example, gripping surface (1426) may include at least one tooth configured to lockingly engage with at least one of rib (128) of cannula (120). Depth limiter (1410) may be disposable

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A depth limiter configured for use with a surgical cannula, the depth limiter comprising: (a) an annular base including: (i) an underside configured to be positioned against a patient, and (ii) a boss extending about a longitudinal axis of the depth limiter, wherein the boss has a boss lumen configured to receive the surgical cannula therethrough; and (b) a latch arm coupled with the annular base, wherein the latch arm overlies the boss and includes an arm opening configured to align with the boss lumen to receive the surgical cannula therethrough, wherein the latch arm is selectively movable relative to the annular base between a release position and a lock position, wherein in the release position the arm opening is positioned coaxially with the boss lumen such that the latch arm is configured to permit longitudinal movement of the depth limiter along the surgical cannula, wherein in the lock position the arm opening is positioned non-coaxially with the boss lumen such that the latch arm is configured to engage an outer surface of the surgical cannula and thereby inhibit longitudinal movement of the depth limiter along the surgical cannula.

Example 2

The depth limiter of Example 1, wherein the release position is a proximal position and the lock position is a distal position.

Example 3

The depth limiter of any of the preceding Examples, wherein the latch arm is resiliently biased away from the release position and toward the lock position.

Example 4

The depth limiter of any of the preceding Examples, wherein the latch arm comprises a spring arm.

Example 5

The depth limiter of any of the preceding Examples, wherein the latch arm includes an upwardly curved lip configured to be engaged by a user to transition the latch arm from the release position to the lock position.

Example 6

The depth limiter of any of the preceding Examples, wherein the latch arm includes a first arm portion extending away from the annular base and a second arm portion extending from the first arm portion towards the central axis.

Example 7

The depth limiter of Example 6, wherein the second arm portion is configured to extend perpendicularly to the longitudinal axis when the latch arm is in the release position.

Example 8

The depth limiter of any of the preceding Examples, wherein the boss is configured to limit a maximum deflection angle of the latch arm in a direction toward the annular base.

Example 9

The depth limiter of Example 8, wherein the boss includes a proximal face, wherein the proximal face is obliquely positioned relative to the longitudinal axis and is configured to engage the latch arm at the maximum deflection angle.

Example 10

The depth limiter of any of the preceding Examples, wherein the annular base includes a pair of relief cut features adjacent to a base end of the latch arm coupled to the annular base, wherein the relief cut features are configured to promote deflection of the latch arm relative to the annular base.

Example 11

The depth limiter of any of the preceding Examples, wherein the latch arm includes an edge that defines a portion of the arm opening, wherein the edge is configured to engage a side portion of the surgical cannula to thereby maintain the latch arm in the lock position.

Example 12

The depth limiter of Example 11, wherein the edge is configured to mate with a tissue engagement feature of the surgical cannula.

Example 13

The depth limiter of any of the preceding Examples, wherein the annular base includes a rolled outer edge.

Example 14

The depth limiter of any of the preceding Examples, wherein each of the boss lumen and the arm opening has the same transverse cross-sectional shape.

Example 15

The depth limiter of any of the preceding Examples, wherein the lock position comprises a first lock position, wherein the latch arm is biased toward the first lock position and is movable toward the annular base from the first lock position to a second lock position, wherein in the second lock position the arm opening is non-coaxial with the boss opening to a greater degree than when in the first lock position.

Example 16

The depth limiter of Example 15, wherein the latch arm is configured to directly contact the boss in the second lock position.

Example 17

A surgical access device assembly comprising: (a) a cannula having a working channel configured to guide a surgical instrument along a longitudinal axis of the cannula; and (b) a depth limiter movably coupled with the cannula, the depth limiter including: (i) a base having a passage that extends through the base along a passage axis, and (ii) a latch arm coupled with the base, wherein the latch arm overlies the passage and includes an arm opening having an opening axis, wherein the cannula is slidably disposed within the passage and the arm opening, wherein the latch arm is selectively movable relative to the base between a release position and a lock position, wherein in the release position the opening axis is aligned with the passage axis such that the depth limiter is configured to freely translate longitudinally along the cannula, wherein in the lock position the opening axis is not aligned with the passage axis such that the latch arm is configured to engage an outer surface of the cannula and thereby fix the depth limiter longitudinally relative to the cannula.

Example 18

The surgical access device assembly of Example 17, wherein the latch arm is resiliently biased toward the lock position.

Example 19

The surgical access device assembly of any of Examples 17 through 18, wherein the base includes a proximal face configured to abut the latch arm in the lock position and thereby limit a range of motion of the latch arm in a direction toward the base.

Example 20

A depth limiter configured for use with a surgical cannula, the depth limiter comprising: (a) a base including: (i) an underside configured to be positioned against a patient, and (ii) a boss extending about a longitudinal axis of the depth limiter, wherein the boss has a proximal face and a boss lumen configured to receive the surgical cannula therethrough; and (b) a latch arm coupled with the base, wherein the latch arm overlies the boss and includes an arm opening configured to align with the boss lumen to receive the surgical cannula therethrough, wherein the latch arm is selectively movable relative to the base between a proximal release position and a distal lock position, wherein in the proximal release position the arm opening is positioned coaxially with the boss lumen such that the latch arm is configured to permit the depth limiter to translate along the surgical cannula, wherein in the distal lock position the latch arm is configured to abut the proximal face of the boss and the arm opening is positioned non-coaxially with the boss lumen such that the latch arm is configured to engage an outer surface of the surgical cannula and thereby inhibit translation of the depth limiter relative to the surgical cannula.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 17/213,302, entitled "Pinch-To-Release Cannula Depth Limiter," filed on Mar. 26, 2021, issued as U.S. Pat. No. 11,633,211 on Apr. 25, 2023; U.S. patent application Ser. No. 17/213,304, entitled "Multi-Diameter Cannula Depth Limiter," filed on Mar. 26, 2021, published as U.S. Pub. No. 2021/0338281 on Nov. 4, 2021; U.S. patent application Ser. No. 17/213,401, entitled "Pinch-To-Clamp Cannula Depth Limiter," filed on Mar. 26, 2021, published as U.S. Pub. No. 2021/0338273 on Nov. 4, 2021; U.S. patent application Ser. No. 17/213,409, entitled "Universal Size Multi-Walled Elastomer Cannula Depth Limiter," filed on Mar. 26, 2021, published as U.S. Pub. No. 2021/0338282 on Nov. 4, 2021; U.S. patent application Ser. No. 17/213,415, entitled "Threaded Cannula Depth Limiter," filed on Mar. 26, 2021, published as U.S. Pub. No. 2021/0338274 on Nov. 4, 2021; U.S. patent application Ser. No. 17/213,431, entitled "Two Piece Separable Obturator," filed on Mar. 26, 2021, published as U.S. Pub. No. 2021/0338275 on Nov. 4, 2021; U.S. patent application Ser. No. 17/213,434, entitled "Latchless Obturator with Interference Fit Feature," filed on Mar. 26, 2021, published as U.S. Pub. No. 2021/0338269 on Nov. 4, 2021; U.S. patent application Ser. No. 17/213,437, entitled "Balancing Feature for Reusable Trocar," filed on Mar. 26, 2021, issued as U.S. Pat. No. 11,559,329 on Jan. 24, 2023; U.S. patent application Ser. No. 17/213,508, entitled "Airflow Channels and Patterns in Lumen for Cannula," filed on Mar. 26, 2021, published as U.S. Pub. No. 2021/0338278 on Nov. 4, 2021; and/or U.S. patent application Ser. No. 17/213,518, entitled "Stabilizer for Surgical Shafts or Cannulas," filed on Mar. 26, 2021, published as U.S. Pub. No. 2021/0338371 on Nov. 4, 2021. The disclosure of each of these patent applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A depth limiter configured for use with a surgical cannula, the depth limiter comprising:
 (a) an annular base including:
  (i) an underside configured to be positioned against a patient, and
  (ii) a boss extending about a longitudinal axis of the depth limiter, wherein the boss has a boss lumen configured to receive the surgical cannula therethrough; and
 (b) a latch arm coupled with the annular base, wherein the latch arm overlies the boss and includes an arm opening configured to align with the boss lumen to receive the surgical cannula therethrough,
 wherein the latch arm is selectively movable relative to the annular base between a release position and a lock position,
 wherein in the release position the arm opening is positioned coaxially with the boss lumen such that the latch arm is configured to permit longitudinal movement of the depth limiter along the surgical cannula,
 wherein in the lock position the arm opening is positioned non-coaxially with the boss lumen such that the latch arm is configured to engage an outer surface of the surgical cannula and thereby inhibit longitudinal movement of the depth limiter along the surgical cannula.

2. The depth limiter of claim 1, wherein the release position is a proximal position and the lock position is a distal position.

3. The depth limiter of claim 1, wherein the latch arm is resiliently biased away from the release position and toward the lock position.

4. The depth limiter of claim 1, wherein the latch arm comprises a spring arm.

5. The depth limiter of claim 1, wherein the latch arm includes an upwardly curved lip configured to be engaged by a user to transition the latch arm from the release position to the lock position.

6. The depth limiter of claim 1, wherein the latch arm includes a first arm portion extending away from the annular base and a second arm portion extending from the first arm portion towards the central axis.

7. The depth limiter of claim 6, wherein the second arm portion is configured to extend perpendicularly to the longitudinal axis when the latch arm is in the release position.

8. The depth limiter of claim 1, wherein the boss is configured to limit a maximum deflection angle of the latch arm in a direction toward the annular base.

9. The depth limiter of claim 8, wherein the boss includes a proximal face, wherein the proximal face is obliquely positioned relative to the longitudinal axis and is configured to engage the latch arm at the maximum deflection angle.

10. The depth limiter of claim 1, wherein the annular base includes a pair of relief cut features adjacent to a base end of the latch arm coupled to the annular base, wherein the relief cut features are configured to promote deflection of the latch arm relative to the annular base.

11. The depth limiter of claim 1, wherein the latch arm includes an edge that defines a portion of the arm opening, wherein the edge is configured to engage a side portion of the surgical cannula to thereby maintain the latch arm in the lock position.

12. The depth limiter of claim 11, wherein the edge is configured to mate with a tissue engagement feature of the surgical cannula.

13. The depth limiter of claim 1, wherein the annular base includes a rolled outer edge.

14. The depth limiter of claim 1, wherein each of the boss lumen and the arm opening has the same transverse cross-sectional shape.

15. The depth limiter of claim 1, wherein the lock position comprises a first lock position, wherein the latch arm is biased toward the first lock position and is movable toward the annular base from the first lock position to a second lock position, wherein in the second lock position the arm opening is non-coaxial with the boss opening to a greater degree than when in the first lock position.

16. The depth limiter of claim 15, wherein the latch arm is configured to directly contact the boss in the second lock position.

17. A surgical access device assembly comprising:
 (a) a cannula having a working channel configured to guide a surgical instrument along a longitudinal axis of the cannula; and
 (b) a depth limiter movably coupled with the cannula, the depth limiter including:
  (i) a base having a passage that extends through the base along a passage axis, and
  (ii) a latch arm coupled with the base, wherein the latch arm overlies the passage and includes an arm opening having an opening axis, wherein the cannula is slidably disposed within the passage and the arm opening,
 wherein the latch arm is selectively movable relative to the base between a release position and a lock position,
 wherein in the release position the opening axis is aligned with the passage axis such that the depth limiter is configured to freely translate longitudinally along the cannula,
 wherein in the lock position the opening axis is not aligned with the passage axis such that the latch arm is configured to engage an outer surface of the cannula and thereby fix the depth limiter longitudinally relative to the cannula.

18. The surgical access device assembly of claim 17, wherein the latch arm is resiliently biased toward the lock position.

19. The surgical access device assembly of claim 17, wherein the base includes a proximal face configured to abut the latch arm in the lock position and thereby limit a range of motion of the latch arm in a direction toward the base.

20. A depth limiter configured for use with a surgical cannula, the depth limiter comprising:
 (a) a base including:
  (i) an underside configured to be positioned against a patient, and
  (ii) a boss extending about a longitudinal axis of the depth limiter, wherein the boss has a proximal face and a boss lumen configured to receive the surgical cannula therethrough; and
 (b) a latch arm coupled with the base, wherein the latch arm overlies the boss and includes an arm opening configured to align with the boss lumen to receive the surgical cannula therethrough,
 wherein the latch arm is selectively movable relative to the base between a proximal release position and a distal lock position, wherein in the proximal release position the arm opening is positioned coaxially with the boss lumen such that the latch arm is configured to permit the depth limiter to translate along the surgical cannula, wherein in the distal lock position the latch arm is configured to abut the proximal face of the boss and the arm opening is positioned non-coaxially with the boss lumen such that the latch arm is configured to engage an outer surface of the surgical cannula and thereby inhibit translation of the depth limiter relative to the surgical cannula.

\* \* \* \* \*